US007220720B2

(12) United States Patent
Bednarek

(10) Patent No.: US 7,220,720 B2
(45) Date of Patent: May 22, 2007

(54) MELANIN-CONCENTRATING HORMONE ANALOGS

(75) Inventor: Maria A. Bednarek, Colonia, NJ (US)

(73) Assignee: Merk & Co., Inc., Rahway, NJ (US)

( * ) Notice: Subject to any disclaimer, the term of this patent is extended or adjusted under 35 U.S.C. 154(b) by 82 days.

(21) Appl. No.: 10/182,509

(22) PCT Filed: Feb. 1, 2001

(86) PCT No.: PCT/US01/03293

§ 371 (c)(1),
(2), (4) Date: Jul. 31, 2002

(87) PCT Pub. No.: WO01/57070

PCT Pub. Date: Aug. 9, 2001

(65) Prior Publication Data

US 2003/0105278 A1  Jun. 5, 2003

Related U.S. Application Data

(60) Provisional application No. 60/179,967, filed on Feb. 3, 2000.

(51) Int. Cl.
C07K 7/08 (2006.01)
A61K 38/00 (2006.01)
(52) U.S. Cl. .............................. 514/9; 514/13; 514/14; 514/15; 530/300; 530/326; 530/327; 530/334; 530/344; 435/7.1
(58) Field of Classification Search .................... 514/9, 514/13, 14, 15; 530/300, 326, 327, 334; 530/344; 435/7.1
See application file for complete search history.

(56) References Cited

U.S. PATENT DOCUMENTS

| 5,049,655 A | 9/1991 | Vaughan et al. |
| 5,849,708 A | 12/1998 | Maratos-Flier |

FOREIGN PATENT DOCUMENTS

| WO | WO 90/11295 | 10/1990 |

OTHER PUBLICATIONS

Hintermann et al., Innovation and Perspective in Solid Phase Synthesis & Combinatorial Libraries: Peptides, Proteins and Nucleic Acids-Small Molecule Organic Chemical Diversity, Collected Papers, International Symposium, 5th, London, Sep. 2-6, 1997, p. 193-196.*
Audinot, V. et al. "Structure-Activity Relationship Studies of Melanin-concentrating Hormone (MCH)-related Peptide Ligands at SLC-1, the Human MCH Receptor", The Journal of Biological Chemistry, 2001, vol. 276, pp. 13554-13562.
Bachner, D. et al. "Identification of melanin concentrating hormone (MCH) as the natural ligand for the orphan somatostatin-like receptor 1 (SLC-1)", FEBS Letters, 1999, vol. 457, pp. 522-524.
Baker, B. et al. "Structure-Activity Studies With Fragments and Analogues of Salmonid Melanin-Concentrating Hormone", Peptides, 1990, vol. 11, pp. 1103-1108.

Chambers, J. et al. "Melanin-concentrating hormone is the cognate ligand for the orphan G-protein-coupled receptor SLC-1", Nature, 1999, vol. 400, pp. 261-265.
Drozdz, R. et al. "(D-(p-Benzoylphenylalanine)13, Tyrosine19)-Melanin-concentrating Hormone, a Potent Analogue for MCH Receptor Crosslinking", Journal of Peptide Science, 1999, vol. 5, pp. 234-242.
Drozdz, R. et al. "Melanin-concentrating hormone binding to mouse melanoma cells in vitro", FEBS Letters, 1995, vol. 359, pp. 199-202.
Erickson, J. et al. "Sensitivity to leptin and susceptibility to seizures of mice lacking neuropeptide Y", Nature, 1996, vol. 381, pp. 415-421.
Flier, J. et al. "Obesity and the Hypothalamus: Novel Peptides for New Pathways", Cell, 1998, vol. 92, pp. 437-440.
Hintermann, E. et al. "Synthesis and Characterization of New Radioligands for the Mammalian Melanin-Concentrating Hormone (MCH) Receptor", Journal of Receptor & Signal Transduction Research, 1999, vol. 19, pp. 411-422.
Lebl, M. et al. "Melanin Concentrating Hormone Analogues: Contraction of the Cyclic Structure. 1. Angonist Activity", Journal of Medicinal Chemistry, 1988, vol. 31, pp. 949-954.
MacDonald, D. et al. "Molecular Characterization of the Melanin-Concentrating Hormone/Receptor Complex: Identification of Critical Residues Involved in Binding and Activation", Molecular Pharmacology, 2000, vol. 58, pp. 217-225.
Nahon, J. "The Melanin-Concentrating Hormone: from the Peptide to the Gene", Critical Reviews in Neurobiology, 1994, vol. 8, pp. 221-262.
Presse, F. et al. "Structure of the Human Melanin Concentrating Hormone mRNA", Molecular Endocrinology, 1990, vol. 4, pp. 632-637.
Qu, D. et al. "A role for melanin-concentrating hormone in the central regulation of feeding behaviour", Nature, 1996, vol. 380, pp. 243-247.
Saito, Y. et al. "Molecular characterization of the melanin-concentrating-hormone receptor", Nature, 1999, vol. 400, pp. 265-269.
Shimada, M. et al. "Mice lacking melanin-concentrating hormone are hypophagic and lean", Nature, 1998, vol. 396, pp. 670-674.
Shimomura, Y. et al. "Isolation and Identification of Melanin-Concentrating Hormone as the Endogenous Ligand of the SLC-1 Receptor", Biochemical and Biophysical Research Communications, 1999, vol. 261, pp. 622-626.
Vaughan, J. et al. "Characterization of Melanin-Concentrating Hormone from Rat Hypothalamus", Endocrinology, 1989, vol. 125, pp. 1660-1665.
Hintermann, E. et al. "Synthesis and Receptor Binding Activity of Analogues and Fragments of Human Melanin-concentrating Hormone (MCH)", 1999, No. 44, pp. 193-196 (Presented Sep. 2-6, 1997).
Castrucci, A. et al. "Melanin Concentrating Hormone (MCH): The Message Sequence", 1989, vol. 45, pp. 1141-1148.

* cited by examiner

*Primary Examiner*—Chih-Min Kam
(74) *Attorney, Agent, or Firm*—Sheldon O. Herber

(57) ABSTRACT

The present invention features truncated MCH analogs active at the MCH receptor. The truncated MCH analogs are optionally modified peptide derivatives of mammalian MCH. The analogs can bind to the MCH receptor and, preferably, bring about signal transduction. MCH analogs have a variety of different uses including being used as a research tool and being used therapeutically.

18 Claims, 1 Drawing Sheet

ALANINE SCAN OF HUMAN MELANIN-CONCENTRATING HORMONE (hMCH)

| | 1 | 3 | 5 | * | 9 | 11 | 13 | 15 | * | 17 | 19 | |
|---|---|---|---|---|---|---|---|---|---|---|---|---|
| | Asp | Phe | Asp | Met Leu Arg Cys | Met | Leu Gly Arg | Val Tyr Arg | Pro | Cys | Trp Gln | Val | ACID |
| BINDING IC$_{50}$ (nM) | 0.8 | 0.2 | 0.49 | 0.49 0.33 4.5 — | 71 | 0.9 — 169 | 0.9 253 1.4 | 1.9 | — | 0.2 1.1 | 0.3 | |
| FUNCTION EC$_{50}$ (nM) | ND | ND | ND | ND ND ND ND | ND | ND — ND | ND ND ND | ND | — | ND ND | ND | |
| % ACTIVATION (100 nM) | 97.7 | 96.3 | 97.7 | 95.7 90.8 11.4 — | 0 | 86.5 — 3 | 82.9 0 90.4 | 76.3 | — | 100 78.3 | 94.4 | | hMCH    BINDING ASSAY[+], IC$_{50}$ = 0.3nM
AEQUORIN FUNCTIONAL ASSAY[++], EC$_{50}$ = 36nM, 100% ACTIVATION AT 10μM

FIG.1

[+] SPA ASSAY: INHIBITION OF ($^{125}$I-F13, Y19-hMCH BINDING TO THE CLONED HUMAN MCH RECEPTOR (COS-7 CELLS)
[++] FOR AEQUORIN FUNCTIONAL ASSAY, 100% ACTIVATION IS THE BIOLUMINESCENCE VALUE OBTAINED WITH 100 nM MCH.
* SITES OF CYCLIZATION (S—S)
ND—NOT DONE

MELANIN-CONCENTRATING HORMONE ANALOGS

CROSS-REFERENCE TO RELATED APPLICATIONS

The present application is a 371 of PCT/US01/03293, filed Feb. 1, 2001, which claims benefit of U.S. Provisional Patent Applications Ser. No. 60/179,967, filed Feb. 3, 2000, which is hereby incorporated by reference herein.

BACKGROUND OF THE INVENTION

Neuropeptides present in the hypothalamus play a major role in mediating the control of body weight. (Flier, et al., 1998. *Cell*, 92, 437–440.) Melanin-concentrating hormone (MCH) produced in mammals is a cyclic 19-amino acid neuropeptide synthesized as part of a larger pre-prohormone precursor in the hypothalamus which also encodes neuropeptides NEI and NGE. (Nahon, et al., 1990. *Mol. Endocrinol*. 4, 632–637; Vaughan, et al., U.S. Pat. No. 5,049,655; and Vaughan, et al., 1989. *Endocrinology* 125, 1660–1665.) MCH was first identified in salmon pituitary, and in fish MCH affects melanin aggregation thus affecting skin pigmentation. In trout and eels MCH has also been shown to be involved in stress induced or CRF-stimulated ACTH release. (Kawauchi, et al., 1983. *Nature* 305, 321–323.)

In humans two genes encoding MCH have been identified that are expressed in the brain. (Breton, et al., 1993. *Mol. Brain Res*. 18, 297–310.) In mammals MCH has been localized primarily to neuronal cell bodies of the hypothalamus which are implicated in the control of food intake, including perikarya of the lateral hypothalamus and zona inertia. (Knigge, et al., 1996. *Peptides* 17, 1063–1073.)

Pharmacological and genetic evidence suggest that the primary mode of MCH action is to promote feeding (orexigenic). MCH mRNA is up regulated in fasted mice and rats, in the ob/ob mouse and in mice with targeted disruption in the gene for neuropeptide Y (NPY). (Qu, et al., 1996. *Nature* 380, 243–247 and Erickson, et al., 1996. *Nature* 381, 415–418.) Injection of MCH centrally (ICV) stimulates food intake and MCH antagonizes the hypophagic effects seen with α melanocyte stimulating hormone (αMSH). (Qu, et al., 1996. *Nature* 380. 243–247.) MCH deficient mice are lean, hypophagic and have increased metabolic rate. (Shimada, et al., 1998. *Nature* 396, 670–673.) The administration of MCH has been indicated to useful for promoting eating, appetite or the gain or maintenance of weight. (Maratos-Flier, U.S. Pat. No. 5,849,708.)

MCH action is not limited to modulation of food intake as effects on the hypothalamic-pituitary-axis have been reported. (Nahon, 1994. *Critical Rev. in Neurobiol*. 8, 221–262.) MCH may be involved in the body response to stress as MCH can modulate the stress-induced release of CRF from the hypothalamus and ACTH from the pituitary. In addition, MCH neuronal systems may be involved in reproductive or maternal function.

SUMMARY OF THE INVENTION

The present invention features truncated MCH analogs active at the MCH receptor. The truncated MCH analogs are optionally modified peptide derivatives of mammalian MCH. The analogs can bind to the MCH receptor and, preferably, bring about signal transduction. MCH analogs have a variety of different uses including being used as a research tool and being used therapeutically.

Thus, a first aspect of the present invention describes a truncated MCH analog. The truncated MCH analog is an optionally modified peptide having the structure:

$$Z^1-X^1-X^2-X^3-X^4-X^5-X^6-$$
$$-X^7-X^8-X^9-X^{10}-X^{11}-X^{12}-X^{13}-X^{14}-X^{15}-X^{16}-X^{17}-Z^2$$

wherein $X^1$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamnic acid, or a derivative thereof;

$X^2$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof;

$X^3$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid or glutamic acid, or a derivative thereof;

$X^4$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, glutamic acid, or norleucine, or a derivative thereof;

$X^5$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid or glutamic acid, or a derivative thereof;

$X^6$ an optionally present amino acid that, if present is either arginine, alanine, leucine, glycine, lysine, proline, asparagine, serine, histidine, nitroarginine, norleucine, or des-amino-arginine, or a derivative thereof;

$X^7$ is either cysteine, homocysteine, or penicillamine, or a derivative thereof;

$X^8$ is either methionine, norleucine, leucine, isoleucine, valine, methioninesulfoxide, or methioninesulfone, or a derivative thereof;

$X^9$ is either leucine, isoleucine, valine, alanine, methionine, or 5-aminopentanoic acid, or a derivative thereof;

$X^{10}$ is either glycine, alanine, leucine, norleucine, cyclohexylalanine, 5-aminopentanoic acid, asparagine, serine, sarcosine, isobutyric, or gamma-aminobutyric acid, or a derivative thereof;

$X^{11}$ is either arginine, lysine, citrulline, histidine, or nitroarginine, or a derivative thereof;

$X^{12}$ is either valine, leucine, isoleucine, alanine, or methionine, or a derivative thereof;

$X^{13}$ is either phenylalanine, tyrosine, D-(p-benzoylphenylalanine), tryptophan, (1')- and (2')-naphthylalanine, cyclohexylalanine, or mono and multi-substituted phenylalanine wherein each substituent is independently selected from the group consisting of O-alkyl, alkyl, OH, $NO_2$, $NH_2$, F, I, and Br; or a derivative thereof;

$X^{14}$ is either arginine, lysine, histidine, norarginine, or 5-aminopentanoic acid or a derivative thereof;

$X^{15}$ is either proline, alanine, valine, leucine, isoleucine, methionine, sarcosine, or 5-aminopentanoic acid, or a derivative thereof;

$X^{16}$ is either cysteine, homocysteine. or penicillamine, or a derivative thereof;

$X^{17}$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid or glutamic acid, or a derivative thereof;

$Z^1$ is an optionally present protecting group that, if present, is covalently joined to the N-terminal amino group;

$Z^2$ is an optionally present protecting group that, if present, is covalently joined to the C-terminal carboxy group;

or a labeled derivative of said peptide;

or a pharmaceutically acceptable salt of said peptide or of said labeled derivative.

Unless otherwise stated, those amino acids with a chiral center are provided in the L-enantiomer. Reference to "a derivative thereof" refers to the corresponding D-amino acid, N-alkyl-amino acid and β-amino acid.

Another aspect of the present invention describes a method of screening for a compound able to bind a MCH receptor. The method comprises the step of measuring the ability of the compound to effect binding of a truncated MCH analog to either the MCH receptor, a fragment of the receptor comprising a MCH binding site, a polypeptide comprising such a fragment, or a derivative of the polypeptide.

Another aspect of the present invention describes a method for increasing weight in a subject. The method comprises the step of administering to the subject an effective amount of a truncated MCH analog to produce a weight increase.

Another aspect of the present invention describes a method for increasing appetite in a subject. The method comprises the step of administering to the subject an effective amount of a truncated MCH analog to produce an appetite increase.

Another aspect of the present invention describes a method for measuring the ability of a compound to decrease weight or appetite in a subject. The method comprising the steps of:

a) administering to the subject an effective amount of a truncated MCH analog to produce a weight increase or appetite increase, b) administering the compound to the subject, and c) measuring the change in weight or appetite of the subject.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIG. 1 illustrates the results of an alanine scan where different amino acid residues of human MCH (SEQ ID NO: 11) were replaced with alanine. The binding assay was performed by measuring inhibition of ($^{125}$I-tyrosine, phenylalanine$^{13}$)-MCH binding to cloned human MCH receptor (CHO clone). Cyclization sites (S—S) are indicated by "*".

DETAILED DESCRIPTION OF THE INVENTION

Truncated MCH analogs contain about 10 to about 17 groups that are amino acids or amino acid derivatives. Using the present application as a guide truncated MCH analogs can be produced having significant MCH receptor activity, and in some cases having activity equal to or better than naturally occurring mammalian MCH. The smaller size of truncated MCH analogs offers advantages over longer-length MCH such as ease of synthesis and/or increased solubility in physiological buffers.

The MCH receptor is a G-protein coupled receptor that appears to be able to couple to Gi and Gq. Several references describe a receptor that is indicated to be a MCH receptor. (Chambers, et al., 1999. *Nature* 400, 261–265; Saito, et al., 1999. *Nature* 400, 265–269; Bäichner, et al., 1999. *FEBS Letters* 457:522–524; and Shimomura, et al., 1999. *Biochemical and Biophysical Research Communications* 261, 622–626. These references are not admitted to be prior art to the claimed invention.)

The nucleic acid encoding for different variants of a MCH receptor is provided for by SEQ. ID. NOS. 1–3. The encoded amino acid sequences of the variants are provided by SEQ. ID. NOS. 4–6. The variants differ from each other by the presence of additional amino acids at the N-terminal. One or more of these variants may be a physiological MCH receptor.

Significant MCH activity is preferably at least about 50%, at least about 75%, at least about 90%, or at least about 95%, the activity of mammalian MCH as determined by a binding assay or MCH receptor activity assay. Examples of such assays are provided below.

MCH analogs have a variety of different uses including being used as a research tool and being used therapeutically. Research tool applications generally involve the use of a truncated MCH analog and the presence of a MCH receptor or fragment thereof. The MCH receptor can be present in different environments such as a mammalian subject, a whole cell and membrane fragments. Examples of research tool applications of truncated MCH analogs include screening for compounds active at the MCH receptor, determining the presence of the MCH receptor in a sample or preparation, examining the role or effect of MCH, and examining the role or effect of MCH antagonists.

Truncated MCH analogs can be used to screen for both MCH agonists and MCH antagonists. Screening for MCH agonists can be performed, for example, by using a truncated MCH analog in a competition experiment with test compounds. Screening for MCH antagonists can be performed, for example, by using a truncated MCH analog to produce MCH receptor activity and then measuring the ability of a compound to alter MCH receptor activity.

Truncated MCH analogs can be administered to a subject. A "subject" refers to a mammal including, for example, a human, a rat, a mouse, or a farm animal. Reference to subject does not necessarily indicate the presence of a disease or disorder. The term subject includes, for example, mammals being dosed with a truncated MCH analog as part of an experiment, mammals being treated to help alleviate a disease or disorder, and mammals being treated prophylactically to retard or prevent the onset of a disease or disorder.

MCH agonists can be used to achieve a beneficial effect in a subject. For example, a MCH agonist can be used to facilitate a weight gain, maintenance of weight and/or an appetite increase. Such effects are particularly useful for a patient having a disease or disorder, or under going a treatment, accompanied by weight loss. Examples of diseases or disorders accompanied by weight loss include anorexia, AIDS, wasting, cachexia, and frail elderly. Examples of treatments accompanied by weight loss include chemotherapy, radiation therapy, and dialysis.

MCH antagonists can also be used to achieve a beneficial effect in a patient. For example, a MCH antagonist can be used to facilitate weight loss, appetite decrease, weight maintenance, cancer (e.g., colon or breast) treatment, pain reduction, stress reduction and/or treatment of sexual dysfunction.

Truncated MCH Analogs

A truncated MCH analog is an optionally modified peptide having the structure:

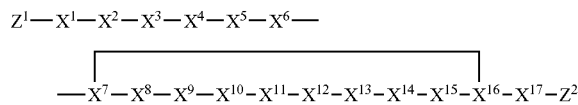

wherein $X^1$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof; preferably, $X^1$ if present is aspartic acid or glutamic acid; more preferably, $X^1$ if present is aspartic acid; and more preferably, $X^1$ is not present;

$X^2$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof; preferably, $X^2$ if present is phenylalanine or tyrosine; more preferably, $X^2$ if present is phenylalanine; and more preferably, $X^2$ is not present;

$X^3$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid or glutamic acid, or a derivative thereof; preferably, $X^3$ if present is aspartic acid or glutamic acid; more preferably, $X^3$ if present is aspartic acid; and more preferably, $X^3$ is not present;

$X^4$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, glutamic acid, or norleucine, or a derivative thereof; preferably, $X^4$ if present is methionine, leucine, isoleucine, valine, alanine or norleucine; more preferably, $X^4$ if present is methionine; and more preferably, $X^4$ is not present;

$X^5$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid or glutamic acid, or a derivative thereof; preferably, $X^5$ if present is leucine, methionine, isoleucine, valine or alanine; more preferably, $X^5$ if present is leucine; and more preferably, $X^5$ is not present;

$X^6$ is an optionally present amino acid that, if present is either arginine, alanine, leucine, glycine, lysine, proline, asparagine, serine, histidine, nitroarginine, norleucine, or des-amino-arginine, or a derivative thereof; preferably $X^6$ is not present or is either arginine, D-arginine, D-norleucine, D-proline, D-serine, or D-asparagine; more preferably $X^6$ is arginine or D-arginine;

$X^7$ is either cysteine, homocysteine, or penicillamine, or a derivative thereof; preferably, $X^7$ is cysteine;

$X^8$ is either methionine, norleucine, leucine, isoleucine, valine, methioninesulfoxide, or methioninesulfone, or a derivative thereof; preferably, $X^8$ is methionine, norleucine, or N-methyl norleucine;

$X^9$ is either leucine, isoleucine, valine, alanine, methionine, or 5-aminopentanoic acid, or a derivative thereof; preferably, $X^9$ is leucine;

$X^{10}$ is either glycine, alanine, leucine, norleucine, cyclohexylalanine, 5-aminopentanoic acid, gamma-aminobutyric acid, asparagine, serine, sarcosine, or isobutyric or a derivative thereof; preferably, $X^{10}$ is either glycine, alanine, leucine, norleucine, asparagine, serine, D-norleucine, D-proline, gamma-aminobutyric acid, or sarcosine; more preferably $X^{10}$, is either glycine, leucine, norlecine, asparagine, or serine;

$X^{11}$ is either arginine, lysine, citrulline, histidine, or nitroarginine, or a derivative thereof; preferably, $X^{11}$ is arginine;

$X^{12}$ is either valine, leucine, isoleucine, alanine, or methionine, or a derivative thereof; preferably, $X^{12}$ is valine;

$X^{13}$ is either phenylalanine, tyrosine, D-(p-benzoylphenylalanine), tryptophan, (1')- and (2')-naphthylalanine, cyclohexylalanine, or mono and multi-substituted phenylalanine wherein each substituent is independently selected from the group consisting of O-alkyl, alkyl, OH, $NO_2$, $NH_2$, F, I, and Br; or a derivative thereof; preferably, $X^{13}$ is phenylalanine. (2')napthylalanine, p-fluoro-phenylalanine, tyrosine, or cyclohexylalanine;

$X^{14}$ is either arginine, lysine, histidine or norarginine, or 5-aminopentanoic acid, or a derivative thereof; preferably, $X^{14}$ is arginine;

$X^{15}$ is either proline, alanine, valine, leucine, isoleucine, methionine, sarcosine, or 5-aminopentanoic acid, or a derivative thereof; preferably, $X^{15}$ is proline or sarcosine;

$X^{16}$ is either cysteine, homocysteine, or penicillamine, or a derivative thereof; preferably, $X^{16}$ is cysteine or D-cysteine;

$X^{17}$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid or glutamic acid, or a derivative thereof; preferably, $X^{17}$ if present is tyrosine or tryptophan; more preferably $X^{17}$ is not present;

$Z^1$ is an optionally present protecting group that, if present, is covalently joined to the N-terminal amino group;

$Z^2$ is an optionally present protecting group that, if present, is covalently joined to the C-terminal carboxy group;

or a labeled derivative of said peptide;

or a pharmaceutically acceptable salt of said peptide or of said labeled derivative.

The present invention is meant to comprehend diastereomers as well as their racemic and resolved enantiomerically pure forms. Truncated MCH analogs can contain D-amino acids, L-amino acids or a combination thereof. Preferably, amino acids present in a truncated MCH analog are the L-enantiomer.

In different embodiments, MCH analogs contain a preferred (or more preferred) group at one or more different locations. More preferred embodiments contain preferred (or more preferred) groups in each of the different locations.

A protecting group covalently joined to the N-terminal amino group reduces the reactivity of the amino terminus under in vivo conditions. Amino protecting groups include optionally substituted —$C_{1-10}$ alkyl, optionally substituted —$C_{2-10}$ alkenyl, optionally substituted aryl, —$C_{1-6}$ alkyl optionally substituted aryl, —C(O)—(CH$_2$)$_{1-6}$—COOH, —C(O)—$C_{1-6}$ alkyl, —C(O)-optionally substituted aryl, —C(O)—O—$C_{1-6}$ alkyl, or —C(O)—O-optionally substituted aryl. Preferably, the amino terminus protecting group is acetyl, propyl, succinyl, benzyl, benzyloxycarbonyl or t-butyloxycarbonyl.

A protecting group covalently joined to the C-terminal carboxy group reduces the reactivity of the carboxy terminus under in vivo conditions. The carboxy terminus protecting group is preferably attached to the α-carbonyl group of the last amino acid. Carboxy terminus protecting groups include amide, methylamide, and ethylamide.

"Alkyl" refers to carbon atoms joined by carbon-carbon single bonds. The alkyl hydrocarbon group may be straight-chain or contain one or more branches or cyclic groups. Preferably, the alkyl group is 1 to 4 carbons in length. Examples of alkyl include methyl, ethyl, propyl, isopropyl, cyclopropyl, butyl, and t-butyl. Alkyl substituents are selected from the group consisting of halogen (preferably —F or —Cl) —OH, —CN, —SH, —NH$_2$, —NO$_2$, —$C_{1-2}$ alkyl substituted with 1 to 6 halogens (preferably —F or —Cl, more preferably —F), —CF$_3$, —OCH$_3$, or —OCF$_3$.

"Alkenyl" refers to a hydrocarbon group containing one or more carbon-carbon double bonds. The alkenyl hydrocarbon group may be straight-chain or contain one or more branches or cyclic groups. Preferably, the alkenyl group is 2 to 4 carbons in length. Alkenyl substituents are selected from the group consisting of halogen (preferably —F or —Cl), —OH, —CN, —SH, —NH$_2$, —NO$_2$, —$C_{1-2}$ alkyl substituted with 1 to 5 halogens (preferably —F or —Cl, more preferably —F), —CF$_3$, —OCH$_3$, or —OCF$_3$.

"Aryl" refers to an optionally substituted aromatic group with at least one ring having a conjugated pi-electron system, containing up to two conjugated or fused ring systems. Aryl includes carbocyclic aryl, heterocyclic aryl and biaryl groups. Preferably, the aryl is a 5 or 6 membered ring, more preferably benzyl. Aryl substituents are selected from the group consisting of —$Cl_{1-4}$ alkyl, —$C_{1-4}$ alkoxy, halogen (preferably —F or —Cl), —OH, —CN, —SH, —NH$_2$, —NO$_2$, —$C_{1-2}$ alkyl substituted with 1 to 5 halogens (preferably —F or —Cl, more preferably —F), —CF$_3$, or —OCF$_3$.

A labeled derivative indicates the alteration of a substituent with a detectable label. Examples of detectable labels include luminescent, enzymatic, and radioactive labels. A preferred radiolabel is $^{125}$I. Both the type of label and the position of the label can effect MCH activity. Labels should be selected so as not to substantially alter the activity of the truncated MCH analog at the MCH receptor. The effect of a particular label on MCH activity can be determined using assays measuring MCH activity and/or binding.

In naturally occurring full length MCH, alteration of the tyrosine at position 13 by labeling with $^{125}$I substantially effects MCH activity. (Drozdz, et al., 1995. *FEBS letters* 359, 199–202.) $^{125}$I labeled analogs of full length mammalian MCH having substantial activity can be produced, for example, by replacing the tyrosine at position 13 with a different group, then replacing valine at position 19 with tyrosine, and labeling the tyrosine. Examples of such analogs include [$^{125}$I][Phe$^{13}$, Try$^{19}$]-MCH and (D-(p-benzoylphenylalanine)$^{13}$, tyrosine$^{19}$)-MCH. (Drozdz, et al., *FEBS letters* 359, 199–202, 1995; and Drozdz, et al., *J. Peptide Sci.* 5, 234–242, 1999.)

In preferred embodiments the optionally modified peptide has the structure:

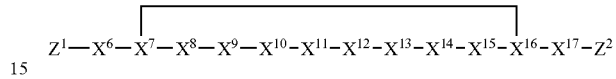

wherein the different groups, and preferred groups, are as described above.

In different embodiments the truncated MCH analog is a peptide of SEQ. ID. NOS. 7, 8, 9, or 10, a labeled derivative of said peptide or a pharmaceutically acceptable salt of said peptide or of said labeled derivative. SEQ. ID. NOS. 7–12 are made up of L-amino acids and have the following sequences ("*" indicates cyclization (S—S)):

```
SEQ. ID. NO. 7:
          *                              *
Ac-Arg-Cys-Met-Leu-Gly-Arg-Val-Tyr-Arg-Pro-Cys-
amide;

SEQ. ID. NO. 8:
          *                                    *
Ac-Arg-Cys-Met-Leu-Gly-Arg-Val-Phe-Arg-Pro-Cys-
Tyr-amide;

SEQ. ID. NO. 9:
      *                                *
Ac-Cys-Met-Leu-Gly-Arg-Val-Tyr-Arg-Pro-Cys-amide;

SEQ. ID. NO. 10:
                      *
Asp-Phe-Asp-Met-Leu-Arg-Cys-Met-Leu-Gly-Arg-Val-
              *
Tyr-Arg-Pro-Cys-amide;

SEQ. ID. NO. 12:
      *                                *
Ac-Cys-Met-Leu-Gly-Arg-Val-Tyr-Arg-Pro-Cys-Trp-
Gln-Val;

SEQ. ID. NO. 13:
                          *
Asp-Phe-Asp-Nle-Leu-Arg-Cys-Nle-Leu-Gly-Arg-Val-
              *
Tyr-Arg-Pro-Cys-Trp-Gln-Val;

SEQ. ID. NO. 14:
                      *
Asp-Phe-Ala-Met-Leu-Arg-Cys-Met-Leu-Gly-Arg-Val-
              *
Phe-Arg-Pro-Cys-Trp-Gln-Tyr.
```

In additional embodiments the peptide has a sequence selected from the group consisting of SEQ. ID. NOs. 7, 8, 10, 15, 24, 25, 27, 28, 30–49, 51, 52, 56, 57, 61, 62, 63, 65–67, 69–72, and 77, is a labeled derivative of said peptide or a pharmaceutically acceptable salt of said peptide or of said labeled derivative. Preferred sequences are those with an IC$_{50}$ less than 0.3 nM, preferably less than 0.1 nM; and/or those having a % activation greater than about 90%, preferably greater than 100%. Examples of preferred sequences are provided in Example 4, Tables 1–7.

Truncated MCH analogs can be produced using techniques well known in the art. For example, a polypeptide region of a truncated MCH analog can be chemically or biochemically synthesized and, if desired modified to produce a blocked N-terminus and/or blocked C-terminus. Techniques for chemical synthesis of polypeptides are well known in the art. (See e.g., Vincent, in *Peptide and Protein Drug Delivery*, New York, N.Y., Dekker, 1990.) Examples of techniques for biochemical synthesis involving the introduction of a nucleic acid into a cell and expression of nucleic acids are provided in Ausubel, *Current Protocols in Molecular Biology*, John Wiley, 1987–1998, and Sambrook, et al., in *Molecular Cloning, A Laboratory Manual*, $2^{nd}$ Edition, Cold Spring Harbor Laboratory Press, 1989.

MCH Receptor Binding Assay

Assays measuring the ability of a compound to bind a MCH receptor employ a MCH receptor, a fragment of the receptor comprising a MCH binding site, a polypeptide comprising such a fragment, or a derivative of the polypeptide. Preferably, the assay uses the MCH receptor or a fragment thereof.

A polypeptide comprising a MCH receptor fragment that binds MCH can also contain one or more polypeptide regions not found in a MCH receptor. A derivative of such a polypeptide comprises a MCH receptor fragment that binds MCH along with one or more non-peptide components.

The MCH receptor amino acid sequence involved in MCH binding can be readily identified using labeled MCH or truncated MCH analogs and different receptor fragments. Different strategies can be employed to select fragments to be tested to narrow down the binding region. Examples of such strategies include testing consecutive fragments about 15 amino acids in length starting at the N-terminus, and testing longer length fragments. If longer length fragments are tested, a fragment binding MCH can be subdivided to further locate the MCH binding region. Fragments used for binding studies can be generated using recombinant nucleic acid techniques.

Binding assays can be performed using individual compounds or preparations containing different numbers of compounds. A preparation containing different numbers of compounds having the ability to bind to the MCH receptor can be divided into smaller groups of compounds that can be tested to identify the compound(s) binding to the MCH receptor. In an embodiment of the present invention a test preparation containing at least 10 compounds is used in a binding assay.

Binding assays can be performed using recombinantly produced MCH receptor polypeptides present in different environments. Such environments include, for example, cell extracts and purified cell extracts containing the MCH receptor polypeptide expressed from recombinant nucleic acid or naturally occurring nucleic acid; and also include, for example, the use of a purified MCH receptor poly,peptide produced by recombinant means or from naturally occurring nucleic acid which is introduced into a different environment.

Screening for MCH Receptor Active Compounds

Screening for MCH active compounds is facilitated using a recombinantly expressed MCH receptor. Using recombinantly expressed MCH receptor polypeptides offers several advantages such as the ability to express the receptor in a defined cell system so that response to MCH receptor active compounds can more readily be differentiated from responses to other receptors. For example, the MCH receptor can be expressed in a cell line such as HEK 293, COS 7, and CHO not normally expressing the receptor by an expression vector, wherein the same cell line without the expression vector can act as a control.

Screening for MCH receptor active compounds is facilitated through the use of a truncated MCH analog in the assay. The use of a truncated MCH analog in a screening assay provides for MCH receptor activity. The effect of test compounds on such activity can be measured to identify, for example, allosteric modulators and antagonists. Additionally, such assays can be used to identify agonists.

MCH receptor activity can be measured using different techniques such as detecting a change in the intracellular conformation of the MCH receptor, Gi or Gq activity, and/or intracellular messengers. Gi activity can be measured using techniques well known in the art such as a melonaphore assay, assays measuring cAMP production, inhibition of cAMP accumulation, and binding of $^{35}$S-GTP. cAMP can be measured using different techniques such as radioimmunoassay and indirectly by cAMP responsive gene reporter proteins.

Gq activity can be measured using techniques such as those measuring intracellular $Ca^{2+}$. Examples of techniques well known in the art that can be employed to measure $Ca^{2+}$ include the use of dyes such as Fura-2 and the use of $Ca^{2+}$-bioluminescent sensitive reporter proteins such as aequorin. An example of a cell line employing aequorin to measure G-protein activity is HEK293/aeq17. (Button, et al., 1993. *Cell Calcium* 14, 663–671, and Feighner, et al., 1999. *Science* 284, 2184–2188, both of which are hereby incorporated by reference herein.)

Chimeric receptors containing a MCH binding region functionally coupled to a G protein can also be used to measure MCH receptor activity. A chimeric MCH receptor contains an N-terminal extracellular domain; a transmembrane domain made up of transmembrane regions, extracellular loop regions, and intracellular loop regions; and an intracellular carboxy terminus. Techniques for producing chimeric receptors and measuring G protein coupled responses are provided for in, for example, International Application Number WO 97/05252, and U.S. Pat. No. 5,264,565, both of which are hereby incorporated by reference herein.

Weight or Appetite Alteration

Truncated MCH analogs can be used in methods to increase or maintain weight and/or appetite in a subject. Such methods can be used, for example, as part of an experimental protocol examining the effects of MCH antagonists, to achieve a beneficial effect in a subject and/or to further examine the physiological effects of MCH.

Experimental protocols examining the effects of MCH antagonists can be performed, for example, by using a sufficient amount of a truncated MCH analog to produce a weight or appetite increase in a subject and then examining the effect of a test compound. Changes in weight and appetite can be measured using techniques well known in the art.

Increasing weight or appetite can be useful for maintaining weight or producing a weight or appetite gain in an under weight subject, or in a patient having a disease or undergoing treatment that effects weight or appetite. In addition, for example, farm animals such as pigs, cows and chickens can be treated to gain weight.

Under weight subjects include those having a body weight about 10% or less, 20% or less, or 30% or less, than the lower end of a "normal" weight range or Body Mass Index ("BMI"). "Normal" weight ranges are well known in the art and take into account factors such as a patient age, height, and body type.

BMI measures your height/weight ratio. It is determined by calculating weight in kilograms divided by the square of height in meters. The BMI "normal" range is 19–22.

Administration

Truncated MCH analogs can be formulated and administered to a subject using the guidance provided herein along with techniques well known in the art. The preferred route of administration ensures that an effective amount of compound reaches the target. Guidelines for pharmaceutical administration in general are provided in, for example, *Remington's Pharmaceutical Sciences* 18$^{th}$ Edition, Ed. Gennaro, Mack Publishing, 1990, and *Modern Pharmaceutics* 2$^{nd}$ Edition, Eds. Banker and Rhodes, Marcel Dekker, Inc., 1990, both of which are hereby incorporated by reference herein.

Truncated MCH analogs can be prepared as acidic or basic salts. Pharmaceutically acceptable salts (in the form of water- or oil-soluble or dispersible products) include conventional non-toxic salts or the quaternary ammonium salts that are formed, e.g., from inorganic or organic acids or bases. Examples of such salts include acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine.

Truncated MCH analogs can be administered using different routes including oral, nasal, by injection, transdermal, and transmucosally. Active ingredients to be administered orally as a suspension can be prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants.

Truncated MCH analogs may also be administered in intravenous (both bolus and infusion), intraperitoneal, subcutaneous, topical with or without occlusion, or intramuscular form. When administered by injection, the injectable solution or suspension may be formulated using suitable non-toxic, parenterally-acceptable diluents or solvents, such as Ringer's solution or isotonic sodium chloride solution, or suitable dispersing or wetting and suspending agents, such as sterile, bland, fixed oils, including synthetic mono- or diglycerides, and fatty acids, including oleic acid.

Suitable dosing regimens are preferably determined taking into factors well known in the art including type of subject being dosed; age, weight, sex and medical condition of the subject; the route of administration; the renal and hepatic function of the subject; the desired effect; and the particular compound employed.

Optimal precision in achieving concentrations of drug within the range that yields efficacy without toxicity requires a regimen based on the kinetics of the drug's availability to target sites. This involves a consideration of the distribution, equilibrium, and elimination of a drug. The daily dose for a subject is expected to be between 0.01 and 1,000 mg per subject per day.

Truncated MCH analogs can be provided in kit. Such a kit typically contains an active compound in dosage forms for administration. A dosage form contains a sufficient amount of active compound such that a weight or appetite increase can be obtained when administered to a subject during regular intervals, such as 1 to 6 times a day, during the course of 1 or more days. Preferably, a kit contains instructions indicating the use of the dosage form for weight or appetite increase and the amount of dosage form to be taken over a specified time period.

EXAMPLES

Examples are provided below to further illustrate different features of the present invention. The examples also illustrate useful methodology for practicing the invention. These examples do not limit the claimed invention.

Example 1

Synthesis of MCH Analogs

MCH analogs were produced using the procedures described below and varying the stepwise addition of amino acid groups. Other procedures for producing and modifying peptides are well known in the art.

Elongation of peptidyl chains on 4-(2',4'-dimethoxyphenyl-Fmoc-aminomethyl)-phenoxy resin and the acetylation of the N-terminal amino groups of the peptides was performed on a 431A ABI peptide synthesizer. Manufacture-supplied protocols were applied for coupling of the hydroxybenzotriazole esters of amino acids in N-methylpyrrolidone (NMP). The fluorenylmethyloxycarbonyl (Fmoc) group was used as a semipermanent alpha-amino protecting group, whereas the side chains protecting groups were: tert-butyl for aspartic acid and tyrosine, 2,2,4,6,7-pentamethyldihydrobenzofuran-5-sulfonyl (Pbf) for arginine, and trityl for cysteine.

Peptides were cleaved from the resin with TFA containing 5% of anisole. After 2 hours at room temperature the resin was filtered, washed with TFA and the combined filtrates were evaporated to dryness in vacuo. The residue was triturated with ether, the precipitate which formed was filtered off washed with ether, and dried.

Crude peptides were dissolved in 5% acetic acid in water, and the pH of the solutions were adjusted to ca. 8.2 with diluted ammonium hydroxide. The reaction mixtures were stirred vigorously while 0.05% solution of potassium ferricyanide ($K_3Fe(CN)_6$) in water was added dropwise till the reaction mixture remained yellow for about 5 minutes. After an additional 20 minutes oxidation was terminated with ca. 1 ml of acetic acid and the reaction mixtures were lyophilized.

Crude lyophilized peptides were analyzed by analytical reverse-phase high-pressure liquid chromatography (RP HPLC) on a C18 Vydac column attached to a Waters 600E system with automatic Wisp 712 injector and 991 Photodiode Array detector. A standard gradient system of 0–100% buffer B in 30 minutes was used for analysis: buffer A was 0.1% trifluoroacetic acid in water and buffer B was 0.1% trifluoroacetic acid in acetonitrile. HPLC profiles were recorded at 210 nm and 280 nm. Preparative separations were performed on a Waters Delta Prep 4000 system with a semipreparative C18 RP Waters column. The above-described solvent system of water and acetonitrile, in a gradient of 20–80% buffer B in 60 minutes, was used for separation. The chromatographically homogenous compounds were analyzed by electrospray mass spectrometry.

Example 2

Aequorin Bioluminescence Functional Assay

The aequorin bioluminescence assay is a reliable test for measuring the activity of G protein-coupled receptors that couple through the Gα protein subunit family consisting of Gq and G11 and leads to the activation of phospholipase C, mobilization of intracellular calcium and activation of protein kinase C.

Measurement of MCH receptor activity in the aequorin-expressing stable reporter cell line 293-AEQ17 (Button et al., Cell Calcium 14:663–671, 1993) was performed using a Luminoskan RT luminometer (Labsystems Inc., Gaithersburg, Md.). 293-AEQ17 cells ($8 \times 10^5$ cells plated 18 hours before transfection in a T75 flask) were transfected with 22 µg of human MCH receptor plasmid using 264 µg lipofectamine. The open reading frame cDNA (SEQ. ID. NO. 1) encoding the human MCH receptor inserted in the mammalian expression vector pcDNA-3 (Invitrogen, Carlsbad, Calif.) was used for expression studies. Following approximately 40 hours of expression the apo-aequorin in the cells was charged for 4 hours with coelenterazine (10 µM) under reducing conditions (300 µM reduced glutathione) in ECB buffer (140 mM NaCl, 20 mM KCl, 20 mM HEPES-NaOH [pH=7.4], 5 mM glucose, 1 mM $MgCl_2$, 1 mM $CaCl_2$, 0.1 mg/ml bovine serum albumin).

The cells were harvested, washed once in ECB medium and resuspended to 500,000 cells/ml. 100 µl of cell suspension (corresponding to $5 \times 10^4$ cells) was then injected into the test plate containing MCH or MCH analogs, and the integrated light emission was recorded over 30 seconds, in 0.5 second units. 20 µL of lysis buffer (0.1% final Triton X-100 concentration) was then injected and the integrated light emission recorded over 10 seconds, in 0.5 second units. The "fractional response" values for each well were calculated by taking the ratio of the integrated response to the initial challenge to the total integrated luminescence including the Triton X-100 lysis response.

Example 3

Radiolabeled MCH-R Binding Assay

Activity of truncated MCH analogs was assayed by measuring the ability of the analog to inhibit binding of [$^{125}$I]-human MCH (Phe$^{13}$, Tyr$^{19}$ substituted) to membranes prepared from cells stably expressing the human MCH receptor. Human MCH (Phe$^{13}$, Tyr$^{19}$ substituted) used in the assay was radiolabeled with $^{125}$I at $^{19}$Tyr to a specific activity of ~2000 Ci/mmol (NEN Life Science Products, Boston, Mass.).

Cell membranes were prepared on ice. Each T-75 flask was rinsed twice with 10 ml of Enzyme-free Cell Dissociation Buffer (Specialty Media, Lavallette, N.J.), and the cell monolayer was detached in an additional 10 ml of Enzyme-free Cell Dissociation Buffer by incubation at room temperature for 10 minutes. Dissociated cells were centrifuged (500×g for 10 minutes at 4° C.), resuspended in 5 ml homogenization buffer (10 mM Tris-HCl, pH 7.4, 0.01 mM Pefabloc, 10 µM phosphoramidon, 40 µg/ml bacitracin) and then homogenized using a glass homogenizer (10–15 strokes). The homogenate was centrifuged for 10 minutes (1,000×g at 4° C.). The resulting supernatant was then centrifuged at 38,700×g for 15 minutes at 4° C. Pelleted membranes were resuspended (passed through 25 gauge needle 5 times), snap-frozen on liquid nitrogen, and stored at −80° C. until use.

Binding was performed in a 96-well filter assay or Scintillation Proximity Assay (SPA)-based format using cell membranes from a stable CHO or HEK-293 cell line expressing the MCH receptor. For the filter assay, reactions were performed at 20° C. for 1 hour in a total volume of 0.2 ml containing: 0.05 ml of membrane suspension (~3 µg protein), 0.02 ml of [$^{125}$I]-human MCH (Phe$^{13}$, Tyr$^{19}$ substituted; 30 pM), 0.01 ml of competitor and 0.12 ml of binding buffer (50 mM Tris-HCl, pH 7.4, 10 mM $MgCl_2$, 2 mM EDTA, 200 µg/ml bacitracin, 1 µM phosphoramidon).

Bound radioligand was separated by rapid vacuum filtration (Packard Filtermate 96-well cell harvester) through GF/C filters pretreated for 1 hour with 1% polyethylenimine. After application of the membrane suspension to the filter, the filters were washed 3 times with 3 ml each of ice-cold 50 mM Tris-HCl, pH 7.4, 10 mM $MgCl_2$, 2 mM EDTA, 0.04% Tween 20 and the bound radioactivity on the filters was quantitated by scintillation counting (TopCount device). Specific binding (>80% of total) is defined as the difference between total binding and non-specific binding conducted in the presence of 100 nM unlabeled human MCH.

For the SPA-based assay, WGA-PVT beads (NEN Life Sciences Products) were resuspended in Dulbecco's PBS with calcium and magnesium (500 mg beads in 4 ml PBS). For each 96-well assay plate, 0.18 ml of beads was pre-coated with MCH receptor by mixing with 0.2 ml MCH receptor CHO cell membranes (~0.2–4 mg protein) and 1.5 ml SPA assay buffer (50 mM Tris-HCl, pH 7.4, 10 mM $MgCl_2$, 2 mM EDTA, 0.1% BSA, 12% glycerol). The suspension was mixed gently for 20 minutes, 12.3 ml of assay buffer and protease inhibitors were added (final concentration given): 2 µg/ml leupeptin, 10 µM phosphoramidon, 40 µg/ml bacitracin, 5 µg/ml aprotinin, 0.1 mM Pefabloc.

Coated beads were kept on ice until use. For each well, 0.145 ml of beads were added to Optiplate assay plates (Packard 6005190), followed by 0.002–0.004 ml of competitor and 0.05 ml of [$^{125}$I]-human MCH (Phe$^{13}$, Tyr$^{19}$ substituted; 30 pM). Binding reactions were allowed to proceed at room temperature for 3 hours. Quantitation was performed by scintillation counting (TopCount device).

Example 4

MCH Activity

The activity of different MCH analogs was measured using the procedures described in Examples 2 and 3 above. Tables 1–7 illustrate the activity of different truncated MCH analogs and mammalian MCH (SEQ. ID. NO. 11). FIG. 1 illustrates the results of replacing different amino acids of mammalian MCH with alanine. Based on the guidance provided herein, additional MCH analogs active at the MCH receptor can be obtained.

TABLE 1

|  | Binding Assay | | |
|---|---|---|---|
| SEQ. ID. NO. | $IC_{50}$ (nM) | $EC_{50}$ (nM) | % Activation at 10 μM |
| 11 | 0.3 | 36 | 100 |
| 7 | 0.12 | 18 | 123 |
| 8 | 0.16 | 36 | 123 |
| 9 | 1.6 | 300 | 74 |
| 10 | 0.3 |  | 99 |
| 12 | 6.4 | 492 | 3 |
| 13 | 1.5 |  | 65.9 |
| 14 | 0.5 |  | 62.2 |

$IC_{50}$ was determined using a SPA based assay.
$EC_{50}$ (nM) and % Activation at 10 μM were determined using aequorin functional assays.

Table 2 illustrates the affect of different D-amino acids.

TABLE 2

$Ac\text{-}Arg^6\text{-}Cys^7\text{-}Met^8\text{-}Leu^9\text{-}Gly^{10}\text{-}Arg^{11}\text{-}Val^{12}\text{-}Tyr^{13}\text{-}Arg^{14}\text{-}Pro^{15}\text{-}Cys^{16}\text{-}NH_2$

|  |  | Activity | | |
|---|---|---|---|---|
| SEQ. ID. NO. | Compound | $IC_{50}$ (nM) | $EC_{50}$ (nM) | Activation % |
| 11 |  | 0.3 | 30.9 | 100 |
| 7 |  | 0.5 | 20 | 99 |
| 15 | D-Arg⁶ | 0.46 | 45 | 86 |
| 16 | D-Cys⁷ | 7.78 | 909 | 34 |
| 17 | D-Met⁸ | >1000 | Inactive |  |
| 18 | D-Leu⁹ | 1520 | Inactive |  |
| 19 | D-Arg¹¹ | >1000 | Inactive |  |
| 20 | D-Val¹² | 381 | Inactive |  |
| 21 | D-Tyr¹³ | >1000 | Inactive |  |
| 22 | D-Arg¹⁴ | 368 | Inactive |  |
| 23 | D-Pro¹⁵ | 584 | Inactive |  |
| 24 | D-Cys¹⁶ | 0.8 | 133 | 76 |

Table 3 illustrates the effect of different N-methyl-amino acids.

TABLE 3

$Ac\text{-}Arg^6\text{-}Cys^7\text{-}Met^8\text{-}Leu^9\text{-}Gly^{10}\text{-}Arg^{11}\text{-}Val^{12}\text{-}Tyr^{13}\text{-}Arg^{14}\text{-}Pro^{15}\text{-}Cys^{16}\text{-}NH_2$

|  |  | Activity | | |
|---|---|---|---|---|
| SEQ. ID. NO. | Compound | $IC_{50}$ (nM) | $EC_{50}$ (nM) | Activation % |
| 11 |  | 0.3 | 30.9 | 100 |
| 7 |  | 1.4 | 20 | 99 |
| 25 | N-Me-Nle⁸ | 0.16 | 20 | 110 |
| 26 | N-Me-Leu⁹ | 10% @ 1 | >10000 | 3 |
| 27 | Sar¹⁰ | 2.3 | 140 | 95 |
| 28 | N-Me-Arg¹¹ | 43 | 10 | 110 |
| 29 | N-Me-Arg¹⁴ | 643 | >1000 |  |
| 30 | Sar¹⁵ | 0.36 | 25 | 113 |

Table 4 illustrates the affect of different alterations to position 6 of the SEQ. ID. NO. 7 MCH analog.

TABLE 4

$X^6\text{-}Cys^7\text{-}Met^8\text{-}Leu^9\text{-}Gly^{10}\text{-}Arg^{11}\text{-}Val^{12}\text{-}Tyr^{13}\text{-}Arg^{14}\text{-}Pro^{15}\text{-}Cys^{16}\text{-}NH_2$

|  |  | Activity | | |
|---|---|---|---|---|
| SEQ. ID. NO. | Position 6 modification | $IC_{50}$ (nM) | $EC_{50}$ (nM) | Activation % |
| 11 |  | 0.3 | 30.9 | 100 |
| 7 |  | 1.4 | 20 | 99 |
| 31 | Ac-Ala | 27 | 114 | 135 |
| 32 | Ac-Nle | 40 | 117 | 107 |
| 33 | Ac-Pro | 3.4 | 59 | 133 |
| 34 | Ac-Asn | 2.6 | 150 | 96 |
| 35 | Ac-Ser | 4.5 | 207 | 120 |
| 36 | Ac-Glu | 19 | 935 | 113 |
| 37 | H | 12 | 809 | 120 |
| 38 | Ac | 1.6 | 144 | 82 |
| 39 | Arg | 0.13 | 14 | 106 |
| 40 | Δ NH₂-Arg | 0.48 | 38.5 | 49 |
| 41 | Ac-D-Arg | 0.46 | 45 | 86 |
| 42 | Ac-D-Nle | 1.2 | 110 | 97 |
| 43 | Ac-D-Pro | 0.82 | 60 | 96 |
| 44 | Ac-D-Asn | 3 | 340 | 94 |
| 45 | Ac-D-Ser | 2.3 | 170 | 93 |
| 46 | Ac-D-Glu | 8 | 820 | 85 |

Table 5 illustrates the affect of different alterations to position 10 of the SEQ. ID. NO. 7 MCH analog.

TABLE 5

$Ac\text{-}Arg^6\text{-}Cys^7\text{-}Met^8\text{-}Leu^9\text{-}X^{10}\text{-}Arg^{11}\text{-}Val^{12}\text{-}Tyr^{13}\text{-}Arg^{14}\text{-}Pro^{15}\text{-}Cys^{16}\text{-}NH_2$

|  |  | Activity | | |
|---|---|---|---|---|
| SEQ. ID. NO. | Position 10 modification | $IC_{50}$ (nM) | $EC_{50}$ (nM) | Activation % |
| 11 |  | 0.3 | 30.9 | 100 |
| 7 |  | 0.5 | 20 | 99 |
| 47 | Ala | 0.59 | 31 | 104 |
| 48 | Leu | 0.06 | 23 | 106 |
| 49 | Nle | 0.04 | 15 | 106 |
| 50 | Pro | 700 | 519 | 4 |
| 51 | Asn | 0.23 | 23 | 106 |
| 52 | Ser | 0.32 | 65 | 104 |
| 53 | Lys | 110 | 4500 | 25 |
| 54 | Glu | 190 | >10000 | 12 |
| 55 | D-Leu | 16 | 750 | 23 |
| 56 | D-Nle | 2.4 | 215 | 33 |
| 57 | D-Pro | 1.2 | 190 | 90 |
| 58 | D-Glu | 40% @ 1 | >10000 |  |
| 59 | D-Lys | >1000 | >10000 |  |
| 60 | β-Ala | 390 | >1000 | 3.2 |
| 61 | γ-Abu | 2.1 | 30.6 | 101 |

Table 6 illustrates the affect of different alterations to position 13 of the SEQ. ID. NO. 7 MCH analog.

TABLE 6

$Ac\text{-}Arg^6\text{-}Cys^7\text{-}Met^8\text{-}Leu^9\text{-}Gly^{10}\text{-}Arg^{11}\text{-}Val^{12}\text{-}Tyr^{13}\text{-}Arg^{14}\text{-}Pro^{15}\text{-}Cys^{16}\text{-}NH_2$

|  |  | Activity | | |
|---|---|---|---|---|
| SEQ. ID. NO. | Position 13 modification | $IC_{50}$ (nM) | $EC_{50}$ (nM) | Activation % |
| 11 |  | 0.3 | 30.9 | 100 |
| 7 |  | 1.4 | 20 | 99 |
| 62 | Phe | 1 | 46 | 96 |

TABLE 6-continued

Ac-Arg[6]-Cys[7]-Met[8]-Leu[9]-Gly[10]-Arg[11]-Val[12]-Tyr[13]-Arg[14]-Pro[15]-Cys[16]-NH$_2$

| SEQ. ID. NO. | Position 13 modification | Activity IC$_{50}$ (nM) | EC$_{50}$ (nM) | Activation % |
|---|---|---|---|---|
| 63 | Trp | 3.8 | 890 | 83 |
| 64 | His | 13.1 | 3400 | 66 |
| 65 | (2')Nal | 0.15 | 54 | 105 |
| 66 | Phe(pF) | 0.6 | 108 | 98 |
| 67 | Phe(pNH2) | 3.2 | 610 | 88 |
| 68 | Phe(pCOOH) | >1000 | >10000 | |
| 69 | Cha | 0.09 | 122 | 93 |

Table 7 illustrates the affect of some alteration combinations and some alterations to position 8 of the SEQ. ID. NO. 7 MCH analog.

TABLE 7

Ac-Arg[6]-Cys[7]-Met[8]-Leu[9]-Gly[10]-Arg[11]-Val[12]-Tyr[13]-Arg[14]-Pro[15]-Cys[16]-NH$_2$

| SEQ. ID. NO. | Compound | Activity IC$_{50}$ (nM) | EC$_{50}$ (nM) | Activation % |
|---|---|---|---|---|
| 11 | | 0.3 | 30.9 | 100 |
| 7 | | 1.4 | 20 | 99 |
| 70 | Ava[9,10] | 3.7 | 587 | 82 |
| 71 | D-Arg[6],Ava[9,10] | 3.7 | 1080 | 72 |
| 72 | Ava[14,15] | 6.2 | 406 | 75 |
| 73 | D-Arg[6],Ava[14,15] | 19.5 | 1300 | 28 |
| 74 | D-Pro[10],Ava[14,15] | 700 | 1530 | 3 |
| 75 | ΔArg[6],Ava[14,15] | 250 | >10000 | 3 |
| 76 | Ava[9,10],Ava[14,15] | 50 | >10000 | 3 |
| 77 | Nle[8] | 0.5 | 44 | 105 |
| 78 | ΔArg[6],D-Nle[10] | 25 | 72 | 4 |

Other embodiments are within the following claims. While several embodiments have been shown and described, various modifications may be made without departing from the spirit and scope of the present invention.

What is claimed is:

1. An optionally substituted peptide consisting of the structure:

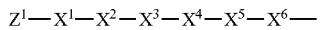
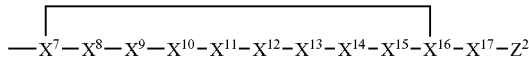

wherein $X^1$, $X^2$, $X^3$, $X^4$, $X^5$ and $X^{17}$ is not present;

$X^6$ is either arginine, alanine, leucine, glycine, lysine, proline, asparagine, serine, histidine, nitroarginine, norleucine, or des-amino-arginine, or a derivative thereof, wherein said derivative is a corresponding D-amino acid, $X^7$ is either cysteine, homocysteine, or penicillamine, or a derivative thereof, wherein said derivative is a corresponding D-amino acid;

$X^8$ is either methionine, norleucine, leucine, isoleucine, valine, methioninesulfoxide, or methioninesulfone, or a derivative thereof, wherein said derivative is a corresponding N-alkyl-amino acid;

$X^9$ is either leucine, isoleucine, valine, alanine, or methionine;

$X^{10}$ is either glycine, alanine, leucine, norleucine, cyclohexylalanine, asparagine, serine, sarcosine, gamma-aminobutyric acid, D-leucine, D-norleucine, or D-proline, or a derivative thereof, wherein said derivative is a corresponding N-alkyl-amino acid;

$X^{11}$ is either arginine, lysine, citrulline, histidine, or nitroarginine, or a derivative thereof, wherein said derivative is a corresponding N-alkyl-amino acid;

$X^{12}$ is either valine, leucine, isoleucine, alanine, or methionine;

$X^{13}$ is either phenylalanine, tyrosine, D-(p-benzoylphenylalanine), tryptophan, (1')- and (2')-naphthylalanine, cyclohexylalanine, or mono and multi-substituted phenylalanine wherein each substituent is independently selected from the group consisting of O-alkyl, alkyl, OH, $NO_2$, $NH_2$, F, I, and Br;

$X^{14}$ is either arginine, lysine, histidine, or norarginine;

$X^{15}$ is either proline, alanine, valine, leucine, isoleucine, methionine, or sarcosine;

$X^{16}$ is either cysteine, homocysteine, or penicillamine, or a derivative thereof, wherein said derivative is a corresponding D-amino acid;

$Z^1$ is an optionally present protecting group that, if present, is covalently joined to the N-terminal amino group;

$Z^2$ is an optionally present protecting group that, if present, is covalently joined to the C-terminal carboxy group;

or a labeled derivative of said peptide;

or a pharmaceutically acceptable salt of said peptide or of said labeled derivative.

2. The peptide of claim 1, wherein said detectable label, if present, is $^{125}I$.

3. The peptide of claim 2, wherein said peptide does not contain said detectable label.

4. The peptide of claim 3, wherein $Z^1$ is —C(O)CH$_3$ and $Z^2$ is —NH$_2$.

5. The peptide of claim 3, wherein said peptide is either SEQ ID NO: 28, 31, 32, 33, 34, 35, 40, 63 or 67; or a pharmaceutically acceptable salt of said peptide.

6. A method of screening for a compound able to bind a melanin-concentrating hormone receptor comprising the steps of:
a) providing to said receptor, said compound and the peptide of claim 2, and
b) measuring the ability of said compound to inhibit binding of said peptide to said receptor, wherein if said compound inhibits binding of said peptide to said receptor then said compound is identified as able to bind to said receptor.

7. An optionally modified peptide consisting of the structure:

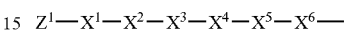
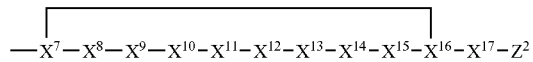

wherein $X^1$, $X^2$, $X^3$, $X^4$, $X^5$ and $X^{17}$ are not present;

$X^6$ is either arginine, D-arginine, D-norleucine, D-proline, D-serine, or D-asparagine;

$X^7$ is cysteine;

$X^8$ is either methionine, norleucine, or N-methyl norleucine;

$X^9$ is leucine;

$X^{10}$ is either glycine, alanine, leucine, norleucine, asparagine, serine, D-norleucine, D-proline, gamma-aminobutyric acid, or sarcosine;

$X^{11}$ is arginine;

$X^{12}$ is valine;

$X^{13}$ is phenylalanine, (2')napthylalanine, p-fluoro-phenylalanine, tyrosine, or cyclohexylalanine;

$X^{14}$ is arginine;

$X^{15}$ is either proline or sarcosine;

$X^{16}$ is either cysteine or D-cysteine;

$Z^1$ is an optionally present protecting group that, if present, is covalently joined to the N-terminal amino group;

$Z^2$ is an optionally present protecting group that if present, is covalently joined to the C-terminal carboxy group;

or a labeled derivative of said peptide;

or a pharmaceutically acceptable salt of said peptide or of said labeled derivative.

8. The peptide of claim 7, wherein said detectable label, if present, is either a radiolabel or luminescent label.

9. The peptide of claim 8, wherein said peptide is either SEQ ID NO: 7, 15, 24, 25, 27, 30, 39, 42, 43, 44, 45, 47, 48, 49, 51, 52, 56, 57, 62, 65, 66, or 77; said labeled derivative of said peptide; or a pharmaceutically acceptable salt of said peptide or of said labeled derivative, wherein said labeled derivative if present is said radiolabel.

10. The peptide of claim 9, wherein said peptide is SEQ ID NO: 7, said labeled derivative of said peptide; or a pharmaceutically acceptable salt of said peptide or of said labeled derivative.

11. A method of screening for a compound able to bind a melanin-concentrating hormone receptor comprising the steps of:
a) providing to said receptor, said compound and the peptide of claim 8; and
b) measuring the ability of said compound to inhibit binding of said peptide to said receptor, wherein if said compound inhibits binding of said peptide to said receptor then said compound is identified as able to bind to said receptor.

12. A method of screening for a compound able to bind a melanin-concentrating hormone receptor comprising the steps of:
   a) providing to said receptor, said compound and the peptide of claim 9, and
   b) measuring the ability of said compound to inhibit binding of said peptide to said receptor, wherein if said compound inhibits binding of said peptide to said receptor then said compound is identified as able to bind to said receptor.

13. A peptide analog consisting of the structure:

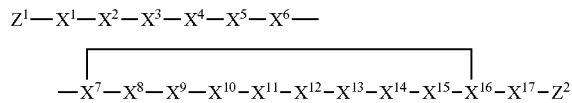

wherein $X^1$, $X^2$, $X^3$, $X^4$, $X^5$ and $X^{17}$ are not present;
$X^6$ is either arginine, D-arginine, D-norleucine, D-proline, D-serine, or D-asparagine;
$X^7$ is cysteine;
$X^8$ is either methionine, norleucine, or N-methyl norleucine;
$X^9$ is leucine;
$X^{10}$ is either glycine, alanine, leucine, norleucine, asparagine, serine, D-norleucine, D-proline, gamma-aminobutyric acid, or sarcosine;
$X^{11}$ is arginine;
$X^{12}$ is valine;
$X^{13}$ is phenylalanine, (2')napthylalanine, p-fluoro-phenylalanine, tyrosine, or cyclohexylalanine;
$X^{14}$ is arginine;
$X^{15}$ is either proline or sarcosine;
$X^{16}$ is either cysteine or D-cysteine;
$Z^1$ is an optionally present protecting group that, if present, is covalently joined to the N-terminal amino group;
$Z^2$ is an optionally present protecting group that, if present, is covalently joined to the C-terminal carboxy group;
or a pharmaceutically acceptable salt of said peptide.

14. The peptide of claim 13, wherein said peptide is either SEQ ID NO: 7, 15, 24, 25, 27, 30, 39, 42, 43, 44, 45, 47, 48, 49, 51, 52, 56, 57, 62, 65, 66 or 77; or a pharmaceutically acceptable salt thereof.

15. The peptide of claim 14, wherein said peptide is either SEQ ID NO: 7 or a pharmaceutically acceptable salt thereof.

16. An optionally substituted peptide consisting of the amino acid sequence of SEQ ID NO: 8 or a labeled derivative thereof, or a pharmaceutically acceptable salt of said peptide or of said labeled derivative.

17. The peptide of claim 16, wherein said peptide consists of the amino acid sequence of SEQ ID NO: 8.

18. A method of screening for a compound able to bind a melanin-concentrating hormone receptor comprising the steps of:
   a) providing to said receptor, said compound and the peptide of claim 16; and
   b) measuring the ability of said compound to inhibit binding of said peptide to said receptor, wherein if said compound inhibits binding of said peptide to said receptor then said compound is identified as able to bind to said receptor.

* * * * *

SEQUENCE LISTING

<160> NUMBER OF SEQ ID NOS: 78

<210> SEQ ID NO 1
<211> LENGTH: 1062
<212> TYPE: DNA
<213> ORGANISM: Human

<400> SEQUENCE: 1

```
atggacctgg aagcctcgct gctgcccact ggtcccaacg ccagcaacac ctctgatggc      60
cccgataacc tcacttcggc aggatcacct cctcgcacgg ggagcatctc ctacatcaac     120
atcatcatgc cttcggtgtt cggcaccatc tgcctcctgg gcatcatcgg gaactccacg     180
gtcatcttcg cggtcgtgaa gaagtccaag ctgcactggt gcaacaacgt ccccgacatc     240
ttcatcatca acctctcggt agtagatctc ctctttctcc tgggcatgcc cttcatgatc     300
caccagctca tgggcaatgg ggtgtggcac tttggggaga ccatgtgcac cctcatcacg     360
gccatggatg ccaatagtca gttcaccagc acctacatcc tgaccgccat ggccattgac     420
cgctacctgg ccactgtcca ccccatctct tccacgaagt tccggaagcc ctctgtggcc     480
accctggtga tctgcctcct gtgggccctc tccttcatca gcatcacccc tgtgtggctg     540
tatgccagac tcatcccctt cccaggaggt gcagtgggct gcggcatacg cctgcccaac     600
ccagacactg acctctactg gttcacccctg taccagtttt tcctggcctt tgccctgcct     660
tttgtggtca tcacagccgc atacgtgagg atcctgcagc gcatgacgtc ctcagtggcc     720
cccgcctccc agcgcagcat ccggctgcgg acaaagaggg tgacccgcac agccatcgcc     780
atctgtctgg tcttctttgt gtgctgggca ccctactatg tgctacagct gacccagttg     840
tccatcagcc gcccgaccct caccttttgtc tacttataca atgcggccat cagcttgggc     900
tatgccaaca gctgcctcaa ccccttttgtg tacatcgtgc tctgtgagac gttccgcaaa     960
cgcttggtcc tgtcggtgaa gcctgcagcc cagggcagc ttcgcgctgt cagcaacgct    1020
cagacggctg acgaggagag gacagaaagc aaaggcacct ga                       1062
```

<210> SEQ ID NO 2
<211> LENGTH: 1254
<212> TYPE: DNA
<213> ORGANISM: Human

<400> SEQUENCE: 2

| | | | | | |
|---|---|---|---|---|---|
| atgaagaagg | gagtggggag | ggcagttggg | cttggaggcg | gcagcggctg | ccaggctacg | 60 |
| gaggaagacc | cccttcccaa | ctgcggggct | tgcgctccgg | acaaggtgg | caggcgctgg | 120 |
| aggctgccgc | agcctgcgtg | gtggagggg | agctcagctc | ggttgtggga | gcaggcgacc | 180 |
| ggcactggct | ggatggacct | ggaagcctcg | ctgctgccca | ctggtcccaa | cgccagcaac | 240 |
| acctctgatg | cccccgataa | cctcacttcg | gcaggatcac | ctcctcgcac | ggggagcatc | 300 |
| tcctacatca | acatcatcat | gccttcggtg | ttcggcacca | tctgcctcct | gggcatcatc | 360 |
| gggaactcca | cggtcatctt | cgcggtcgtg | aagaagtcca | agctgcactg | gtgcaacaac | 420 |
| gtccccgaca | tcttcatcat | caacctctcg | gtagtagatc | tcctctttct | cctgggcatg | 480 |
| cccttcatga | tccaccagct | catgggcaat | ggggtgtggc | actttgggga | gaccatgtgc | 540 |
| accctcatca | cggccatgga | tgccaatagt | cagttcacca | gcacctacat | cctgaccgcc | 600 |
| atggccattg | accgctacct | ggccactgtc | cacccatct | cttccacgaa | gttccggaag | 660 |
| ccctctgtgg | ccaccctggt | gatctgcctc | tgtgggccc | tctccttcat | cagcatcacc | 720 |
| cctgtgtggc | tgtatgccag | actcatcccc | ttcccaggag | gtgcagtggg | ctgcggcata | 780 |
| cgcctgccca | acccagacac | tgacctctac | tggttcaccc | tgtaccagtt | tttcctggcc | 840 |
| tttgccctgc | cttttgtggt | catcacagcc | gcatacgtga | ggatcctgca | gcgcatgacg | 900 |
| tcctcagtgg | cccccgcctc | ccagcgcagc | atccggctgc | ggacaaagag | ggtgacccgc | 960 |
| acagccatcg | ccatctgtct | ggtcttcttt | gtgtgctggg | cacctactac | tgtgctacag | 1020 |
| ctgacccagt | tgtccatcag | ccgcccgacc | ctcacctttg | tctacttata | caatgcggcc | 1080 |
| atcagcttgg | gctatgccaa | cagctgcctc | aaccccttg | tgtacatcgt | gctctgtgag | 1140 |
| acgttccgca | aacgcttggt | cctgtcggtg | aagcctgcag | cccaggggca | gcttcgcgct | 1200 |
| gtcagcaacg | ctcagacggc | tgacgaggag | aggacagaaa | gcaaaggcac | ctga | 1254 |

<210> SEQ ID NO 3
<211> LENGTH: 1269
<212> TYPE: DNA
<213> ORGANISM: Human

<400> SEQUENCE: 3

| | | | | | |
|---|---|---|---|---|---|
| atgtcagtgg | gagccatgaa | gaagggagtg | gggagggcag | ttgggcttgg | aggcggcagc | 60 |
| ggctgccagg | ctacggagga | agaccccctt | cccaactgcg | gggcttgcgc | tccgggacaa | 120 |
| ggtggcaggc | gctggaggct | gccgcagcct | gcgtgggtgg | agggagctc | agctcggttg | 180 |
| tgggagcagg | cgaccggcac | tggctggatg | gacctggaag | cctcgctgct | gcccactggt | 240 |
| cccaacgcca | gcaacacctc | tgatggcccc | gataacctca | cttcggcagg | atcacctcct | 300 |
| cgcacgggga | gcatctccta | catcaacatc | atcatgcctt | cggtgttcgg | caccatctgc | 360 |
| ctcctgggca | tcatcgggaa | ctccacggtc | atcttcgcgg | tcgtgaagaa | gtccaagctg | 420 |
| cactggtgca | acaacgtccc | cgacatcttc | atcatcaacc | tctcggtagt | agatctcctc | 480 |
| tttctcctgg | gcatgccctt | catgatccac | cagctcatgg | gcaatggggt | gtggcacttt | 540 |
| ggggagacca | tgtgcaccct | catcacggcc | atggatgcca | atagtcagtt | caccagcacc | 600 |
| tacatcctga | ccgccatggc | cattgaccgc | tacctggcca | ctgtccaccc | catctcttcc | 660 |

-continued

```
acgaagttcc ggaagccctc tgtggccacc ctggtgatct gcctcctgtg ggccctctcc      720
ttcatcagca tcacccctgt gtggctgtat gccagactca tcccttccc aggaggtgca       780 gtgggctgcg gcatacgcct gcccaaccca gacactgacc tctactggtt caccctgtac      840 cagttttcc tggcctttgc cctgcctttt gtggtcatca cagccgcata cgtgaggatc       900
ctgcagcgca tgacgtcctc agtggccccc gcctcccagc gcagcatccg gctgcggaca      960
aagagggtga cccgcacagc catcgccatc tgtctggtct tctttgtgtg ctgggcaccc     1020
tactatgtgc tacagctgac ccagttgtcc atcagccgcc cgaccctcac ctttgtctac     1080
ttatacaatg cggccatcag cttgggctat gccaacagct gcctcaaccc ctttgtgtac     1140
atcgtgctct gtgagacgtt ccgcaaacgc ttggtcctgt cggtgaagcc tgcagcccag     1200
gggcagcttc gcgctgtcag caacgctcag acggctgacg aggagaggac agaaagcaaa     1260
ggcacctga                                                            1269
```

<210> SEQ ID NO 4
<211> LENGTH: 353
<212> TYPE: PRT
<213> ORGANISM: Human

<400> SEQUENCE: 4

```
Met Asp Leu Glu Ala Ser Leu Leu Pro Thr Gly Pro Asn Ala Ser Asn
 1               5                  10                  15

Thr Ser Asp Gly Pro Asp Asn Leu Thr Ser Ala Gly Ser Pro Pro Arg
             20                  25                  30

Thr Gly Ser Ile Ser Tyr Ile Asn Ile Ile Met Pro Ser Val Phe Gly
         35                  40                  45

Thr Ile Cys Leu Leu Gly Ile Ile Gly Asn Ser Thr Val Ile Phe Ala
     50                  55                  60

Val Val Lys Lys Ser Lys Leu His Trp Cys Asn Asn Val Pro Asp Ile
 65                  70                  75                  80

Phe Ile Ile Asn Leu Ser Val Val Asp Leu Leu Phe Leu Leu Gly Met
                 85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255
```

```
Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
            275                 280                 285

Phe Val Tyr Leu Tyr Asn Ala Ala Ile Ser Leu Gly Tyr Ala Asn Ser
        290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Ala
                325                 330                 335

Val Ser Asn Ala Gln Thr Ala Asp Glu Glu Arg Thr Glu Ser Lys Gly
            340                 345                 350

Thr

<210> SEQ ID NO 5
<211> LENGTH: 417
<212> TYPE: PRT
<213> ORGANISM: Human

<400> SEQUENCE: 5

Met Lys Lys Gly Val Gly Arg Ala Val Gly Leu Gly Gly Gly Ser Gly
  1               5                  10                  15

Cys Gln Ala Thr Glu Glu Asp Pro Leu Pro Asn Cys Gly Ala Cys Ala
            20                  25                  30

Pro Gly Gln Gly Gly Arg Arg Trp Arg Leu Pro Gln Pro Ala Trp Val
        35                  40                  45

Glu Gly Ser Ser Ala Arg Leu Trp Glu Gln Ala Thr Gly Thr Gly Trp
 50                  55                  60

Met Asp Leu Glu Ala Ser Leu Leu Pro Thr Gly Pro Asn Ala Ser Asn
 65                  70                  75                  80

Thr Ser Asp Gly Pro Asp Asn Leu Thr Ser Ala Gly Ser Pro Pro Arg
                85                  90                  95

Thr Gly Ser Ile Ser Tyr Ile Asn Ile Ile Met Pro Ser Val Phe Gly
            100                 105                 110

Thr Ile Cys Leu Leu Gly Ile Ile Gly Asn Ser Thr Val Ile Phe Ala
        115                 120                 125

Val Val Lys Lys Ser Lys Leu His Trp Cys Asn Asn Val Pro Asp Ile
130                 135                 140

Phe Ile Ile Asn Leu Ser Val Val Asp Leu Leu Phe Leu Leu Gly Met
145                 150                 155                 160

Pro Phe Met Ile His Gln Leu Met Gly Asn Gly Val Trp His Phe Gly
                165                 170                 175

Glu Thr Met Cys Thr Leu Ile Thr Ala Met Asp Ala Asn Ser Gln Phe
            180                 185                 190

Thr Ser Thr Tyr Ile Leu Thr Ala Met Ala Ile Asp Arg Tyr Leu Ala
        195                 200                 205

Thr Val His Pro Ile Ser Ser Thr Lys Phe Arg Lys Pro Ser Val Ala
210                 215                 220

Thr Leu Val Ile Cys Leu Leu Trp Ala Leu Ser Phe Ile Ser Ile Thr
225                 230                 235                 240

Pro Val Trp Leu Tyr Ala Arg Leu Ile Pro Phe Pro Gly Gly Ala Val
                245                 250                 255

Gly Cys Gly Ile Arg Leu Pro Asn Pro Asp Thr Asp Leu Tyr Trp Phe
            260                 265                 270
```

```
Thr Leu Tyr Gln Phe Phe Leu Ala Phe Ala Leu Pro Phe Val Ile
        275                 280                 285

Thr Ala Ala Tyr Val Arg Ile Leu Gln Arg Met Thr Ser Ser Val Ala
    290                 295                 300

Pro Ala Ser Gln Arg Ser Ile Arg Leu Arg Thr Lys Arg Val Thr Arg
305                 310                 315                 320

Thr Ala Ile Ala Ile Cys Leu Val Phe Phe Val Cys Trp Ala Pro Tyr
                325                 330                 335

Tyr Val Leu Gln Leu Thr Gln Leu Ser Ile Ser Arg Pro Thr Leu Thr
                340                 345                 350

Phe Val Tyr Leu Tyr Asn Ala Ala Ile Ser Leu Gly Tyr Ala Asn Ser
                355                 360                 365

Cys Leu Asn Pro Phe Val Tyr Ile Val Leu Cys Glu Thr Phe Arg Lys
        370                 375                 380

Arg Leu Val Leu Ser Val Lys Pro Ala Ala Gln Gly Gln Leu Arg Ala
385                 390                 395                 400

Val Ser Asn Ala Gln Thr Ala Asp Glu Glu Arg Thr Glu Ser Lys Gly
                405                 410                 415

Thr

<210> SEQ ID NO 6
<211> LENGTH: 422
<212> TYPE: PRT
<213> ORGANISM: Human

<400> SEQUENCE: 6

Met Ser Val Gly Ala Met Lys Lys Gly Val Gly Arg Ala Val Gly Leu
  1               5                  10                  15

Gly Gly Gly Ser Gly Cys Gln Ala Thr Glu Glu Asp Pro Leu Pro Asn
                 20                  25                  30

Cys Gly Ala Cys Ala Pro Gly Gln Gly Gly Arg Arg Trp Arg Leu Pro
             35                  40                  45

Gln Pro Ala Trp Val Glu Gly Ser Ser Ala Arg Leu Trp Glu Gln Ala
     50                  55                  60

Thr Gly Thr Gly Trp Met Asp Leu Glu Ala Ser Leu Leu Pro Thr Gly
 65                  70                  75                  80

Pro Asn Ala Ser Asn Thr Ser Asp Gly Pro Asp Asn Leu Thr Ser Ala
                 85                  90                  95

Gly Ser Pro Pro Arg Thr Gly Ser Ile Ser Tyr Ile Asn Ile Ile Met
                100                 105                 110

Pro Ser Val Phe Gly Thr Ile Cys Leu Leu Gly Ile Ile Gly Asn Ser
            115                 120                 125

Thr Val Ile Phe Ala Val Val Lys Lys Ser Lys Leu His Trp Cys Asn
    130                 135                 140

Asn Val Pro Asp Ile Phe Ile Ile Asn Leu Ser Val Val Asp Leu Leu
145                 150                 155                 160

Phe Leu Leu Gly Met Pro Phe Met Ile His Gln Leu Met Gly Asn Gly
                165                 170                 175

Val Trp His Phe Gly Glu Thr Met Cys Thr Leu Ile Thr Ala Met Asp
            180                 185                 190

Ala Asn Ser Gln Phe Thr Ser Thr Tyr Ile Leu Thr Ala Met Ala Ile
    195                 200                 205

Asp Arg Tyr Leu Ala Thr Val His Pro Ile Ser Ser Thr Lys Phe Arg
210                 215                 220
```

-continued

```
Lys Pro Ser Val Ala Thr Leu Val Ile Cys Leu Leu Trp Ala Leu Ser
225                 230                 235                 240

Phe Ile Ser Ile Thr Pro Val Trp Leu Tyr Ala Arg Leu Ile Pro Phe
            245                 250                 255

Pro Gly Gly Ala Val Gly Cys Gly Ile Arg Leu Pro Asn Pro Asp Thr
        260                 265                 270

Asp Leu Tyr Trp Phe Thr Leu Tyr Gln Phe Leu Ala Phe Ala Leu
    275                 280                 285

Pro Phe Val Val Ile Thr Ala Ala Tyr Val Arg Ile Leu Gln Arg Met
    290                 295                 300

Thr Ser Ser Val Ala Pro Ala Ser Gln Arg Ser Ile Arg Leu Arg Thr
305                 310                 315                 320

Lys Arg Val Thr Arg Thr Ala Ile Ala Ile Cys Leu Val Phe Phe Val
                325                 330                 335

Cys Trp Ala Pro Tyr Tyr Val Leu Gln Leu Thr Gln Leu Ser Ile Ser
            340                 345                 350

Arg Pro Thr Leu Thr Phe Val Tyr Leu Tyr Asn Ala Ala Ile Ser Leu
        355                 360                 365

Gly Tyr Ala Asn Ser Cys Leu Asn Pro Phe Val Tyr Ile Val Leu Cys
370                 375                 380

Glu Thr Phe Arg Lys Arg Leu Val Leu Ser Val Lys Pro Ala Ala Gln
385                 390                 395                 400

Gly Gln Leu Arg Ala Val Ser Asn Ala Gln Thr Ala Asp Glu Glu Arg
                405                 410                 415

Thr Glu Ser Lys Gly Thr
            420

<210> SEQ ID NO 7
<211> LENGTH: 11
<212> TYPE: PRT
<213> ORGANISM: Artificial Sequence
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: DISULFID
<222> LOCATION: (2)...(11)
<223> OTHER INFORMATION: MCH Analog

<400> SEQUENCE: 7

Arg Cys Met Leu Gly Arg Val Tyr Arg Pro Cys
1               5                   10

<210> SEQ ID NO 8
<211> LENGTH: 12
<212> TYPE: PRT
<213> ORGANISM: Artificial Sequence
<220> FEATURE:
<221> NAME/KEY: ACETYLATION
<222> LOCATION: (1)...(1)
<220> FEATURE:
<221> NAME/KEY: AMIDATION
<222> LOCATION: (12)...(12)
<220> FEATURE:
<221> NAME/KEY: DISULFID
<222> LOCATION: (2)...(11)
<223> OTHER INFORMATION: MCH Analog

<400> SEQUENCE: 8

Arg Cys Met Leu Gly Arg Val Phe Arg Pro Cys Tyr
```

<210> SEQ ID NO 9
<211> LENGTH: 10
<212> TYPE: PRT
<213> ORGANISM: Artificial Sequence
<220> FEATURE:
<221> NAME/KEY: ACETYLATION
<222> LOCATION: (1)...(1)
<220> FEATURE:
<221> NAME/KEY: AMIDATION
<222> LOCATION: (10)...(10)
<220> FEATURE:
<221> NAME/KEY: DISULFID
<222> LOCATION: (1)...(10)
<223> OTHER INFORMATION: MCH Analog

<400> SEQUENCE: 9

Cys Met Leu Gly Arg Val Tyr Arg Pro Cys
1               5                   10

<210> SEQ ID NO 10
<211> LENGTH: 16
<212> TYPE: PRT
<213> ORGANISM: Artificial Sequence
<220> FEATURE:
<221> NAME/KEY: AMIDATION
<222> LOCATION: (16)...(16)
<220> FEATURE:
<221> NAME/KEY: DISULFID
<222> LOCATION: (7)...(16)
<223> OTHER INFORMATION: MCH Analog

<400> SEQUENCE: 10

Asp Phe Asp Met Leu Arg Cys Met Leu Gly Arg Val Tyr Arg Pro Cys
1               5                   10                  15

<210> SEQ ID NO 11
<211> LENGTH: 19
<212> TYPE: PRT
<213> ORGANISM: Human
<220> FEATURE:
<221> NAME/KEY: DISULFID
<222> LOCATION: (7)...(16)

<400> SEQUENCE: 11

Asp Phe Asp Met Leu Arg Cys Met Leu Gly Arg Val Tyr Arg Pro Cys
1               5                   10                  15

Trp Gln Val

<210> SEQ ID NO 12
<211> LENGTH: 13
<212> TYPE: PRT
<213> ORGANISM: Artificial Sequence
<220> FEATURE:
<223> OTHER INFORMATION: MCH Analog
<220> FEATURE:
<221> NAME/KEY: DISULFID
<222> LOCATION: (1)...(10)
<220> FEATURE:
<221> NAME/KEY: ACETYLATION
<222> LOCATION: (1)...(1)

<400> SEQUENCE: 12

Cys Met Leu Gly Arg Val Tyr Arg Pro Cys Trp Gln Val
1               5                   10

<210> SEQ ID NO 13
<211> LENGTH: 19

```
<212> TYPE: PRT
<213> ORGANISM: Artificial Sequence
<220> FEATURE:
<223> OTHER INFORMATION: MCH Analog
<220> FEATURE:
<221> NAME/KEY: DISULFID
<222> LOCATION: (7)...(16)
<220> FEATURE:
<221> NAME/KEY: MOD_RES
<222> LOCATION: (4)...(4)
<223> OTHER INFORMATION: Xaa = Norleucine
<220> FEATURE:
<221> NAME/KEY: MOD_RES
<222> LOCATION: (8)...(8)
<223> OTHER INFORMATION: Xaa = Norleucine

<400> SEQUENCE: 13

Asp Phe Asp Xaa Leu Arg Cys Xaa Leu Gly Arg Val Tyr Arg Pro Cys
 1               5                  10                  15

Trp Gln Val

<210> SEQ ID NO 14
<211> LENGTH: 19
<212> TYPE: PRT
<213> ORGANISM: Artificial Sequence
<220> FEATURE:
<223> OTHER INFORMATION: MCH Analog
<220> FEATURE:
<221> NAME/KEY: DISULFID
<222> LOCATION: (7)...(16)

<400> SEQUENCE: 14

Asp Phe Ala Met Leu Arg Cys Met Leu Gly Arg Val Phe Arg Pro Cys
 1               5                  10                  15

Trp Gln Tyr

<210> SEQ ID NO 15
<211> LENGTH: 11
<212> TYPE: PRT
<213> ORGANISM: Artificial Sequence
<220> FEATURE:
<223> OTHER INFORMATION: MCH Analogs
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: MOD_RES
<222> LOCATION: (1)...(1)
<223> OTHER INFORMATION: Xaa = D-Arginine
<220> FEATURE:
<221> NAME/KEY: AMIDATION
<222> LOCATION: (11)...(11)

<400> SEQUENCE: 15

Xaa Cys Met Leu Gly Arg Val Tyr Arg Pro Cys
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: DISULFID
<222> LOCATION: (2)...(11)
<220> FEATURE:
<221> NAME/KEY: MOD_RES
```

```
<222> LOCATION: (2)...(2)
<223> OTHER INFORMATION: Xaa = D-Cysteine
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 16

Arg Xaa Met Leu Gly Arg Val Tyr Arg Pro Cys
 1               5                   10

<210> SEQ ID NO 17
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: DISULFID
<222> LOCATION: (2)...(11)
<220> FEATURE:
<221> NAME/KEY: MOD_RES
<222> LOCATION: (3)...(3)
<223> OTHER INFORMATION: Xaa = D-Methionine
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 17

Arg Cys Xaa Leu Gly Arg Val Tyr Arg Pro Cys
 1               5                   10

<210> SEQ ID NO 18
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: DISULFID
<222> LOCATION: (2)...(11)
<220> FEATURE:
<221> NAME/KEY: MOD_RES
<222> LOCATION: (4)...(4)
<223> OTHER INFORMATION: Xaa = D-Leucine
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 18

Arg Cys Met Xaa Gly Arg Val Tyr Arg Pro Cys
 1               5                   10

<210> SEQ ID NO 19
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: DISULFID
<222> LOCATION: (2)...(11)
<220> FEATURE:
<221> NAME/KEY: MOD_RES
<222> LOCATION: (6)...(6)
```

```
<223> OTHER INFORMATION: Xaa = D-Arginine
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 19

Arg Cys Met Leu Gly Xaa Val Tyr Arg Pro Cys
 1               5                   10

<210> SEQ ID NO 20
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: DISULFID
<222> LOCATION: (2)...(11)
<220> FEATURE:
<221> NAME/KEY: MOD_RES
<222> LOCATION: (7)...(7)
<223> OTHER INFORMATION: Xaa = D-Valine
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 20

Arg Cys Met Leu Gly Arg Xaa Tyr Arg Pro Cys
 1               5                   10

<210> SEQ ID NO 21
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: DISULFID
<222> LOCATION: (2)...(11)
<220> FEATURE:
<221> NAME/KEY: MOD_RES
<222> LOCATION: (8)...(8)
<223> OTHER INFORMATION: Xaa = D-Tyrosine
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 21

Arg Cys Met Leu Gly Arg Val Xaa Arg Pro Cys
 1               5                   10

<210> SEQ ID NO 22
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (9)...(9)
<223> OTHER INFORMATION: Xaa = D-Arginine
```

```
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 22

Arg Cys Met Leu Gly Arg Val Tyr Xaa Pro Cys
 1               5                   10

<210> SEQ ID NO 23
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (10)...(10)
<223> OTHER INFORMATION: Xaa = D-Proline
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 23

Arg Cys Met Leu Gly Arg Val Tyr Arg Xaa Cys
 1               5                   10

<210> SEQ ID NO 24
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (11)...(11)
<223> OTHER INFORMATION: Xaa = D-Cysteine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 24

Arg Cys Met Leu Gly Arg Val Tyr Arg Pro Xaa
 1               5                   10

<210> SEQ ID NO 25
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (3)...(3)
<223> OTHER INFORMATION: Xaa = N-Me-Norleucine
<220> FEATURE:
```

```
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 25

Arg Cys Xaa Leu Gly Arg Val Tyr Arg Pro Cys
 1               5                  10

<210> SEQ ID NO 26
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (4)...(4)
<223> OTHER INFORMATION: Xaa = N-Me-Leucine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 26

Arg Cys Met Xaa Gly Arg Val Tyr Arg Pro Cys
 1               5                  10

<210> SEQ ID NO 27
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (5)...(5)
<223> OTHER INFORMATION: Xaa = MeGly
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 27

Arg Cys Met Leu Xaa Arg Val Tyr Arg Pro Cys
 1               5                  10

<210> SEQ ID NO 28
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (6)...(6)
<223> OTHER INFORMATION: Xaa = N-Me-Arginine
<220> FEATURE:
<221> NAME/KEY: DISULFID
```

```
<222> LOCATION: (2)...(11)
<220> FEATURE:
<221> NAME/KEY: AMIDATION
<222> LOCATION: (11)...(11)

<400> SEQUENCE: 28

Arg Cys Met Leu Gly Xaa Val Tyr Arg Pro Cys
1               5                   10

<210> SEQ ID NO 29
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (9)...(9)
<223> OTHER INFORMATION: Xaa = N-Me-Arginine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 29

Arg Cys Met Leu Gly Arg Val Tyr Xaa Pro Cys
1               5                   10

<210> SEQ ID NO 30
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (10)...(10)
<223> OTHER INFORMATION: Xaa = MeGly
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 30

Arg Cys Met Leu Gly Arg Val Tyr Arg Xaa Cys
1               5                   10

<210> SEQ ID NO 31
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: DISULFID
<222> LOCATION: (2)...(11)
<220> FEATURE:
<221> NAME/KEY: AMIDATION
<222> LOCATION: (11)...(11)
```

```
<400> SEQUENCE: 31

Ala Cys Met Leu Gly Arg Val Tyr Arg Pro Cys
1               5                   10

<210> SEQ ID NO 32
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = Norleucine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)
<220> FEATURE:
<221> NAME/KEY: ACETYLATION
<222> LOCATION: (1)...(1)

<400> SEQUENCE: 32

Xaa Cys Met Leu Gly Arg Val Tyr Arg Pro Cys
1               5                   10

<210> SEQ ID NO 33
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 33

Pro Cys Met Leu Gly Arg Val Tyr Arg Pro Cys
1               5                   10

<210> SEQ ID NO 34
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 34

Asn Cys Met Leu Gly Arg Val Tyr Arg Pro Cys
1               5                   10

<210> SEQ ID NO 35
<211> LENGTH: 11
<212> TYPE: PRT
```

```
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 35

Ser Cys Met Leu Gly Arg Val Tyr Arg Pro Cys
 1               5                  10

<210> SEQ ID NO 36
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 36

Glu Cys Met Leu Gly Arg Val Tyr Arg Pro Cys
 1               5                  10

<210> SEQ ID NO 37
<211> LENGTH: 10
<212> TYPE: PRT
<213> ORGANISM: Artificial Sequence
<220> FEATURE:
<223> OTHER INFORMATION: MCH Analog
<220> FEATURE:
<221> NAME/KEY: AMIDATION
<222> LOCATION: (10)...(10)
<220> FEATURE:
<221> NAME/KEY: DISULFID
<222> LOCATION: (1)...(10)

<400> SEQUENCE: 37

Cys Met Leu Gly Arg Val Tyr Arg Pro Cys
     1               5                  10

<210> SEQ ID NO 38
<211> LENGTH: 10
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: DISULFID
<222> LOCATION: (1)...(10)
<220> FEATURE:
<221> NAME/KEY: AMIDATION
<222> LOCATION: (10)...(10)

<400> SEQUENCE: 38

Cys Met Leu Gly Arg Val Tyr Arg Pro Cys
```

-continued

```
1               5                   10
```

<210> SEQ ID NO 39
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: AMIDATION
<222> LOCATION: (11)...(11)
<220> FEATURE:
<221> NAME/KEY: DISULFID
<222> LOCATION: (2)...(11)

<400> SEQUENCE: 39

```
    Arg Cys Met Leu Gly Arg Val Tyr Arg Pro Cys
     1               5                  10
```

<210> SEQ ID NO 40
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = Des-Amino-Arginine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 40

```
Xaa Cys Met Leu Gly Arg Val Tyr Arg Pro Cys
 1               5                  10
```

<210> SEQ ID NO 41
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-Arginine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)
<220> FEATURE:
<221> NAME/KEY: ACETYLATION
<222> LOCATION: (1)...(1)

<400> SEQUENCE: 41

```
Xaa Cys Met Leu Gly Arg Val Tyr Arg Pro Cys
 1               5                  10
```

<210> SEQ ID NO 42
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES

```
<222> LOCATION: (1)...(1)
<223> OTHER INFORMATION: Xaa = D-Norleucine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)
<220> FEATURE:
<221> NAME/KEY: ACETYLATION
<222> LOCATION: (1)...(1)

<400> SEQUENCE: 42

Xaa Cys Met Leu Gly Arg Val Tyr Arg Pro Cys
 1               5                  10

<210> SEQ ID NO 43
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-Proline
<220> FEATURE:
<221> NAME/KEY: DISULFID
<222> LOCATION: (2)...(11)
<220> FEATURE:
<221> NAME/KEY: AMIDATION
<222> LOCATION: (11)...(11)
<220> FEATURE:
<221> NAME/KEY: ACETYLATION
<222> LOCATION: (1)...(1)

<400> SEQUENCE: 43

Xaa Cys Met Leu Gly Arg Val Tyr Arg Pro Cys
 1               5                  10

<210> SEQ ID NO 44
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-Asparagine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)
<220> FEATURE:
<221> NAME/KEY: ACETYLATION
<222> LOCATION: (1)...(1)

<400> SEQUENCE: 44

Xaa Cys Met Leu Gly Arg Val Tyr Arg Pro Cys
 1               5                  10

<210> SEQ ID NO 45
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
```

```
<223> OTHER INFORMATION: Xaa = D-Serine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)
<220> FEATURE:
<221> NAME/KEY: ACETYLATION
<222> LOCATION: (1)...(1)

<400> SEQUENCE: 45

Xaa Cys Met Leu Gly Arg Val Tyr Arg Pro Cys
 1               5                  10

<210> SEQ ID NO 46
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-Glutamic Acid
<220> FEATURE:
<221> NAME/KEY: DISULFID
<222> LOCATION: (2)...(11)
<220> FEATURE:
<221> NAME/KEY: AMIDATION
<222> LOCATION: (11)...(11)
<220> FEATURE:
<221> NAME/KEY: ACETYLATION
<222> LOCATION: (1)...(1)

<400> SEQUENCE: 46

Xaa Cys Met Leu Gly Arg Val Tyr Arg Pro Cys
 1               5                  10

<210> SEQ ID NO 47
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: AMIDATION
<222> LOCATION: (11)...(11)
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)

<400> SEQUENCE: 47

Arg Cys Met Leu Ala Arg Val Tyr Arg Pro Cys
 1               5                  10

<210> SEQ ID NO 48
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: DISULFID
```

```
<222> LOCATION: (2)...(11)

<400> SEQUENCE: 48

Arg Cys Met Leu Leu Arg Val Tyr Arg Pro Cys
 1               5                   10

<210> SEQ ID NO 49
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (5)...(5)
<223> OTHER INFORMATION: Xaa = Norleucine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 49

Arg Cys Met Leu Xaa Arg Val Tyr Arg Pro Cys
 1               5                   10

<210> SEQ ID NO 50
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: DISULFID
<222> LOCATION: (2)...(11)

<400> SEQUENCE: 50

Arg Cys Met Leu Pro Arg Val Tyr Arg Pro Cys
 1               5                   10

<210> SEQ ID NO 51
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: DISULFID
<222> LOCATION: (2)...(11)

<400> SEQUENCE: 51

Arg Cys Met Leu Asn Arg Val Tyr Arg Pro Cys
 1               5                   10

<210> SEQ ID NO 52
```

```
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: DISULFID
<222> LOCATION: (2)...(11)

<400> SEQUENCE: 52

Arg Cys Met Leu Ser Arg Val Tyr Arg Pro Cys
 1               5                  10

<210> SEQ ID NO 53
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: DISULFID
<222> LOCATION: (2)...(11)

<400> SEQUENCE: 53

Arg Cys Met Leu Lys Arg Val Tyr Arg Pro Cys
 1               5                  10

<210> SEQ ID NO 54
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: DISULFID
<222> LOCATION: (2)...(11)

<400> SEQUENCE: 54

Arg Cys Met Leu Glu Arg Val Tyr Arg Pro Cys
 1               5                  10

<210> SEQ ID NO 55
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (5)...(5)
<223> OTHER INFORMATION: Xaa = D-Leucine
<220> FEATURE:
```

```
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 55

Arg Cys Met Leu Xaa Arg Val Tyr Arg Pro Cys
 1               5                  10

<210> SEQ ID NO 56
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (5)...(5)
<223> OTHER INFORMATION: Xaa = D-Norleucine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 56

Arg Cys Met Leu Xaa Arg Val Tyr Arg Pro Cys
 1               5                  10

<210> SEQ ID NO 57
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (5)...(5)
<223> OTHER INFORMATION: Xaa = D-Proline
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 57

Arg Cys Met Leu Xaa Arg Val Tyr Arg Pro Cys
 1               5                  10

<210> SEQ ID NO 58
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (5)...(5)
<223> OTHER INFORMATION: Xaa = D-Glutamic Acid
<220> FEATURE:
<221> NAME/KEY: DISULFID
```

```
<222> LOCATION: (2)...(11)
<220> FEATURE:
<221> NAME/KEY: AMIDATION
<222> LOCATION: (11)...(11)

<400> SEQUENCE: 58

Arg Cys Met Leu Xaa Arg Val Tyr Arg Pro Cys
 1               5                   10

<210> SEQ ID NO 59
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (5)...(5)
<223> OTHER INFORMATION: Xaa = D-Lysine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 59

Arg Cys Met Leu Xaa Arg Val Tyr Arg Pro Cys
 1               5                   10

<210> SEQ ID NO 60
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (5)...(5)
<223> OTHER INFORMATION: Xaa = bAla
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 60

Arg Cys Met Leu Xaa Arg Val Tyr Arg Pro Cys
 1               5                   10

<210> SEQ ID NO 61
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (5)...(5)
<223> OTHER INFORMATION: Xaa = Gamma-Aminobutyric Acid
<220> FEATURE:
<221> NAME/KEY: DISULFID
<222> LOCATION: (2)...(11)
```

-continued

```
<220> FEATURE:
<221> NAME/KEY: AMIDATION
<222> LOCATION: (11)...(11)

<400> SEQUENCE: 61

Arg Cys Met Leu Xaa Arg Val Tyr Arg Pro Cys
 1               5                  10

<210> SEQ ID NO 62
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: DISULFID
<222> LOCATION: (2)...(11)

<400> SEQUENCE: 62

Arg Cys Met Leu Gly Arg Val Phe Arg Pro Cys
 1               5                  10

<210> SEQ ID NO 63
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: DISULFID
<222> LOCATION: (2)...(11)

<400> SEQUENCE: 63

Arg Cys Met Leu Gly Arg Val Trp Arg Pro Cys
 1               5                  10

<210> SEQ ID NO 64
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: DISULFID
<222> LOCATION: (2)...(11)

<400> SEQUENCE: 64

Arg Cys Met Leu Gly Arg Val His Arg Pro Cys
 1               5                  10

<210> SEQ ID NO 65
<211> LENGTH: 11
<212> TYPE: PRT
```

```
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (8)...(8)
<223> OTHER INFORMATION: Xaa = (2')Naphthylalanine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 65

Arg Cys Met Leu Gly Arg Val Xaa Arg Pro Cys
 1               5                  10

<210> SEQ ID NO 66
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (8)...(8)
<223> OTHER INFORMATION: Xaa = P-Fluoro-Phenylalanine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 66

Arg Cys Met Leu Gly Arg Val Xaa Arg Pro Cys
 1               5                  10

<210> SEQ ID NO 67
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (8)...(8)
<223> OTHER INFORMATION: Xaa = P-Amino-Phenylalanine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 67

Arg Cys Met Leu Gly Arg Val Xaa Arg Pro Cys
 1               5                  10

<210> SEQ ID NO 68
<211> LENGTH: 11
<212> TYPE: PRT
<213> ORGANISM: Artificial Sequence
```

```
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (8)...(8)
<223> OTHER INFORMATION: Xaa = P-Carboxy-Phenylalanine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 68

Arg Cys Met Leu Gly Arg Val Xaa Arg Pro Cys
 1               5                  10

<210> SEQ ID NO 69
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (8)...(8)
<223> OTHER INFORMATION: Xaa - Cyclohexylalanine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 69

Arg Cys Met Leu Gly Arg Val Xaa Arg Pro Cys
 1               5                  10

<210> SEQ ID NO 70
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (4)...(5)
<223> OTHER INFORMATION: Xaa = 5-Aminopentanoic Acid
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 70

Arg Cys Met Xaa Xaa Arg Val Tyr Arg Pro Cys
 1               5                  10
```

<210> SEQ ID NO 71
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (1)...(1)
<223> OTHER INFORMATION: Xaa = D-Arginine
<220> FEATURE:
<221> NAME/KEY: MOD_RES
<222> LOCATION: (4)...(5)
<223> OTHER INFORMATION: Xaa = 5-Aminopentanoic Acid
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 71

Xaa Cys Met Xaa Xaa Arg Val Tyr Arg Pro Cys
 1               5                  10

<210> SEQ ID NO 72
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (9)...(10)
<223> OTHER INFORMATION: Xaa = 5-Aminopentanoic Acid
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 72

Arg Cys Met Leu Gly Arg Val Tyr Xaa Xaa Cys
 1               5                  10

<210> SEQ ID NO 73
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (1)...(1)
<223> OTHER INFORMATION: Xaa = D-Arginine
<220> FEATURE:
<221> NAME/KEY: MOD_RES
<222> LOCATION: (9)...(10)
<223> OTHER INFORMATION: Xaa = 5-Aminopentanoic Acid
<220> FEATURE:
<221> NAME/KEY: DISULFID
<222> LOCATION: (2)...(11)
<220> FEATURE:
<221> NAME/KEY: AMIDATION

<222> LOCATION: (11)...(11)

<400> SEQUENCE: 73

Xaa Cys Met Leu Gly Arg Val Tyr Xaa Xaa Cys
 1               5                  10

<210> SEQ ID NO 74
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (5)...(5)
<223> OTHER INFORMATION: Xaa = D-Proline
<220> FEATURE:
<221> NAME/KEY: MOD_RES
<222> LOCATION: (9)...(10)
<223> OTHER INFORMATION: Xaa = 5-Aminopentanoic Acid
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 74

Arg Cys Met Leu Xaa Arg Val Tyr Xaa Xaa Cys
 1               5                  10

<210> SEQ ID NO 75
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (1)...(1)
<223> OTHER INFORMATION: Xaa = Des-Amino-Arginine
<220> FEATURE:
<221> NAME/KEY: MOD_RES
<222> LOCATION: (9)...(10)
<223> OTHER INFORMATION: Xaa = 5-Aminopentanoic Acid
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 75

Xaa Cys Met Leu Gly Arg Val Tyr Xaa Xaa Cys
 1               5                  10

<210> SEQ ID NO 76
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION

```
<222> LOCATION: (1)...(1)
<220> FEATURE:
<221> NAME/KEY: MOD_RES
<222> LOCATION: (4)...(5)
<223> OTHER INFORMATION: Xaa = 5-Aminopentanoic Acid
<220> FEATURE:
<221> NAME/KEY: MOD_RES
<222> LOCATION: (9)...(10)
<223> OTHER INFORMATION: Xaa = 5-Aminopentanoic Acid
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 76

Arg Cys Met Xaa Xaa Arg Val Tyr Xaa Xaa Cys
 1               5                  10

<210> SEQ ID NO 77
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (3)...(3)
<223> OTHER INFORMATION: Xaa = Norleucine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 77

Arg Cys Xaa Leu Gly Arg Val Tyr Arg Pro Cys
 1               5                  10

<210> SEQ ID NO 78
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: ACETYLATION
<222> LOCATION: (1)...(1)
<220> FEATURE:
<221> NAME/KEY: MOD_RES
<222> LOCATION: (1)...(1)
<223> OTHER INFORMATION: Xaa = Des-Amino-Arginine
<220> FEATURE:
<221> NAME/KEY: MOD_RES
<222> LOCATION: (5)...(5)
<223> OTHER INFORMATION: Xaa = D-Norleucine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 78

Xaa Cys Met Leu Xaa Arg Val Tyr Arg Pro Cys
 1               5                  10
```